United States Patent
Nordmann et al.

(10) Patent No.: US 9,328,374 B2
(45) Date of Patent: May 3, 2016

(54) SELECTIVE CULTURE MEDIUM AND METHOD FOR DETECTING CARBAPENEM-RESISTANT BACTERIA IN A TEST SAMPLE

(75) Inventors: Patrice Nordmann, Le Kremlin Bicêtre (FR); Laurent Poirel, Le Kremlin Bicêtre (FR); Delphine Girlich, Le Kremlin Bicêtre (FR)

(73) Assignees: Institut National de la Sante et de la Recherche Medicale (INSERM), Paris (FR); UNIVERSITE PARIS SUD, Orsay (FR); ASSISTANCE PUBLIQUE HOPITAUX DE PARIS, Paris (FR)

( * ) Notice: Subject to any disclaimer, the term of this patent is extended or adjusted under 35 U.S.C. 154(b) by 9 days.

(21) Appl. No.: 14/130,605

(22) PCT Filed: Jul. 5, 2012

(86) PCT No.: PCT/EP2012/063123
§ 371 (c)(1),
(2), (4) Date: Mar. 5, 2014

(87) PCT Pub. No.: WO2013/004779
PCT Pub. Date: Jan. 10, 2013

(65) Prior Publication Data
US 2014/0178922 A1  Jun. 26, 2014

Related U.S. Application Data

(60) Provisional application No. 61/507,234, filed on Jul. 13, 2011.

(30) Foreign Application Priority Data

Jul. 5, 2011 (EP) .................................. 11305860

(51) Int. Cl.
*C12Q 1/04* (2006.01)
*C12Q 1/18* (2006.01)

(52) U.S. Cl.
CPC . *C12Q 1/18* (2013.01); *C12Q 1/045* (2013.01)

(58) Field of Classification Search
None
See application file for complete search history.

(56) References Cited

U.S. PATENT DOCUMENTS

2009/0068696 A1* 3/2009 Frimodt-Moller .............. 435/19

OTHER PUBLICATIONS

Lee et al., "Evaluation of the Hodge Test and the Imipenem-EDTA Double-Disk Synergy Test for Differentiating Metallo-SS-Lactamase-Producing Isolates of *Pseudomonas* spp. and *Acinetobacter* spp.", Journal of Clinical Microbiology, Oct. 2003, vol. 41, No. 10, p. 4623-4629.
Thomson, "Extended-Spectrum-SS-Lactamase, AmpC, and Carbapenemase Issues", Journal of Clinical Microbiology, Apr. 2010, vol. 48, No. 4, p. 1019-1025.
Pasteran et al., "Controlling False-Positive Results Obtained with the Hodge and Masuda Assays for Detection of Class A Carbapenemase in Species of Enterobacteriaceae by Incorporating Boronic Acid", Journal of Clinical Microbiology, Apr. 2010, vol. 48, No. 4, p. 1323-1332.
Giske et al., "A Sensitive and Specific Phenotypic Assay for Detection of Metallo-SS-Lactamases and KPC in Klebsiella Pneumoniae with the use of Meropenem Disks Supplemented with Aminophenylboronic Acid, Dipicolinic Acid and Cloxacillin", Clinical Microbiology and Infection, Jun. 28, 2010, Published Online, Whole Article.
Hawkey et al., "Effect of divalent cation in bacteriological media on the susceptibility of Xanthomonas maltophilia to imipenem, with special reference to zinc ions", Journal of Antimicrobial Chemotherapy, Jan. 1, 1993, pp. 47-55, vol. 31, No. 1, Oxford University Press, GB.
Cirak et al., "Effect of zinc concentration on susceptibility of Pseudomonas aeruginosa to meropenem", Journal of Faculty of Pharmacy of Gazi University, Jan. 1, 1997, pp. 110-113, vol. 14, No. 2, Gazi University, Ankara, TR.
Daly et al., "Effect of zinc concentration in Mueller-Hinton agar on susceptibility of Pseudomonas aeruginosa to imipenem", Journal of Clinical Microbiology, Jan. 1, 1997, pp. 1027-1029, vol. 35, No. 4, American Society for Microbiology, Washington, DC, US.
Marchese et al., "In vitro activity of ertapenem against selected respiratory pathogens", Journal of Antimicrobial Chemotherapy, Nov. 2004, pp. 944-951, vol. 54, No. 5.

* cited by examiner

*Primary Examiner* — Renee Claytor
*Assistant Examiner* — Michelle F Paguio Frising
(74) *Attorney, Agent, or Firm* — Whitham, Curtis, Christofferson & Cook, P.C.

(57) ABSTRACT

The present invention relates to a culture medium comprising a carbapenem, a carbapenemase activator and a M-type penicillin. It also relates to a method for detecting carbapenem-resistant bacteria in a test sample using said culture medium.

9 Claims, No Drawings

SELECTIVE CULTURE MEDIUM AND METHOD FOR DETECTING CARBAPENEM-RESISTANT BACTERIA IN A TEST SAMPLE

FIELD OF THE INVENTION

The present invention relates to a selective culture medium and a method for detecting carbapenem-resistant bacteria, in particular carbapenemase producers, in a test sample.

BACKGROUND OF THE INVENTION

Carbapenemase-producing bacteria isolates are increasingly identified throughout the world (1-8). Their early detection is becoming a major issue in the field of clinical microbiology in order to prevent their spread and preserve the efficacy of carbapenems which are becoming the antibiotics of last resort for treating severe infections. Moreover, carbapenemases are usually associated to many other non-beta-lactam resistant determinants giving rise to multidrug and pandrug resistance. Therefore, due to current population exchange and travel, early recognition of carbapenemase producers is becoming mandatory whatever the antibiotic policy or rate of multidrug-resistant nosocomial infections.

The vast majority of acquired carbapenemases belong to three of the four known classes of beta-lactamases, namely Ambler class A, Ambler class B (metallo-beta-lactamases (MBLs)) and Ambler class D (oxacillinases (OXAs)). These three classes of carbapenemases confer clinical resistance to carbapenems. Consequently, carbapenemase-producing bacteria isolates from these three classes have been involved in nosocomial outbreaks (1,2,7,9,10).

The spread of these three distinct classes of carbapenemases varies significantly worldwide. For example, KPC producers (Ambler class A) are identified mostly in the Americas and Southern Europe, while IMP, VIM, NDM-1 (Ambler class B) are extensively identified worldwide with a main reservoir for NDM-1 in the Indian subcontinent. As for OXA-48-like enzymes (Ambler class D), it was first identified in *Klebsiella pneumoniae* in Turkey in 2003, where it is highly prevalent (11). However, OXA-48-producing bacteria, in particular *Enterobacteriaceae*, have also been reported in several other countries such as France, Belgium, United Kingdom, Germany Egypt, India and North Africa suggesting its widespread nature (1,6,12).

As previously mentioned, early recognition of carbapenemase producers is critical to prevent their spread. However, the level of reduced susceptibility to carbapenems may vary significantly among carbapenemase producers making their detection difficult (11,12,13,14,15).

In particular, although OXA-48-like enzymes remain susceptible to extended-spectrum cephalosporins, they confer resistance to penicillins and reduced susceptibility to carbapenems, thereby making the clinical laboratory detection of OXA-48-like producing isolates difficult. In fact, it has been identified in multidrug-resistant isolates, which often accumulate multiple resistance mechanisms, including production of extended-spectrum beta-lactamases (ESBLs). Most carbapenemase producers co-express ESBLs, but several OXA-48-like producing isolates that do not carry ESBL genes may remain susceptible to extended-spectrum cephalosporins (11).

Commercially available media for detecting carbapenemase producers exist. Examples of such media are the carbapenem-containing CHROMagar KPC (CHROMagar company, Paris, France) and the cefpodoxime-containing chromogenic ChromID ESBL medium (bioMerieux, La Balme-les-Grottes, France) which is designed to screen for ESBL producers (16-17). In addition, each medium contains a chromogenic molecule which may contribute to species recognition. The main disadvantage of screening carbapenemase producers using the ChromID ESBL medium is that it cannot detect OXA-48-like producers which are susceptible to cefpodoxime in the absence of co-production of an ESBL (12). In addition, this medium may lack specificity since non-carbapenemase ESBL producers are co-selected on that medium. As for the CHROMagar KPC medium, its main disadvantage is its lack of sensitivity since carbapenemase producers with low level of resistance to carbapenems are not efficiently detected on this medium (12).

Finally, WO 2010/010083 discusses a method for direct detection and differentiation of carbapenem-resistant bacteria in a sample comprising (i) inoculation with said sample of a culture medium comprising at least meropenem and/or ertapenem and at least one chromogenic agent, (ii) incubation of said culture medium under conditions allowing the growth of carbapenem-resistant bacteria, and (iii) detection of colonies formed on said culture medium corresponding to carbapenem-resistant bacteria. The application also discloses a culture medium suitable for use in such a method. However, the culture medium used in this method is neither sensitive enough, nor specific enough to detect carbapenemases producers with reduced susceptibility to carbapenems.

SUMMARY OF THE INVENTION

To facilitate the detection of carbapenem-resistant bacteria in the field of clinical microbiology, and in particular, carbapenemases producers with reduced susceptibility to carbapenems, the Applicant has developed a new reliable and highly sensitive culture medium comprising a combination of a carbapenem, a carbapenemase activator and a M-type penicillin. The advantage of this new medium for the detection of carbapenemase producers is that it is more sensitive and specific than existing media. Furthermore, neither a high level of Minimum Inhibitory Concentrations (MICs) of carbapenems (which is required in the CHROMagar KPC medium) nor co-expression of an Enlarged Spectrum Beta-Lactamases (ESBL) (which is required in the ChromoID ESBL media) is needed. Moreover this medium can be useful for the detection of carbapenemase producers in human faeces which also contain a large amount of ESBL producers and/or a large amount of AmpC cephalosporinases, the latter activity being inhibited by M-type penicillins. This last point could be more relevant in countries with high rates of these types of isolates.

Therefore, the present invention relates to a culture medium comprising a carbapenem, a carbapenemase activator and a M-type penicillin.

The present invention also relates to a method for detecting carbapenem-resistant bacteria in a test sample comprising the following successive steps:

a) inoculating a culture medium as defined herein with said test sample, b) incubating said culture medium under conditions suitable for growth of carbapenem-resistant bacteria, c) detecting colonies formed on said culture medium corresponding to carbapenem-resistant bacteria.

DETAILED DESCRIPTION OF THE INVENTION

Definitions:

As used herein, "test sample" means any liquid or solid material to be tested which may contain carbapenemase-producing bacteria. The preferred test sample is a biological sample.

As used herein, "biological sample" means any biological sample derived from a subject. Examples of such samples include fluids, skin swabs, tissues, cell samples, etc. Preferred biological samples are saliva, whole blood, serum, plasma, urine or faeces.

As used herein, "subject" denotes a mammal, such as a rodent, a feline, a canine, and a primate. Preferably a subject according to the invention is a human.

Culture Medium:

As previously mentioned, early recognition of carbapenemase producers is critical to prevent their spread. However, a difficulty remains in that the level of reduced susceptibility to carbapenems may vary significantly among carbapenemase producers making their detection difficult.

As a solution to this problem, the Applicant has developed a new culture medium which is reliable, highly sensitive and more specific than existing media for the detection of carbapenemase producers.

The present invention therefore relates to a culture medium comprising a carbapenem, an activator of specific types of carbapenemases and a M-type penicillin.

Typically the concentration of carbapenem is comprised between 0.005 to 4 µg/ml. For example, the concentration of carbapenem can be comprised between 0.01, 0.02, 0.05, or 0.1 to 0.1, 0.2, 0.5 or 1 µg/ml, for example between 0.2 and 0.5 µg/ml. For example the carbapenem concentration is about 0.25 µg/ml.

The preferred concentration will typically depend on the carbapenem used.

For ertapenem, the preferred concentration is comprised between 0.1 to 1 µg/ml, preferably between 0.2 and 0.5 µg/ml and more preferably the ertapenem concentration is about 0.25 µg/ml.

For doripenem, the preferred concentration is comprised between 0.01, to 0.1 µg/ml, preferably between 0.015 and 0.05 µg/ml and more preferably the doripenem concentration is about 0.025 µg/ml.

A low concentration of carbapenem will enable the selection of carbapenemases producers with reduced susceptibility to carbapenems, the carbapenemase activator will increase the expression of Ambler Class B producers, while the M-type penicillin will prevent the growth of isolates which are resistant to carbapenems by production of cephalosporinases (and not carbapenemases) (+/−associated to outer membrane permeability defects), thereby reinforcing the selectivity of the medium. Such cephalosporinases are either of type AmpC or with broadened substrate activity, and can be found in species such as *Enterobacter cloacae, Enterobacter aerogenes, Serratia marcescens* (i.e. Ambler Class C producers).

According to the invention, the carbapenem is selected from the group consisting of biapenem, ertapenem, doripenem, imipenem, meropenem, tebipenem, panipenem and mixtures thereof. Preferably the carbapenem is ertapenem.

Based on molecular studies, carbapenemases can be further divided into two types: serine enzymes possessing a serine moiety at the active site (Ambler Class A, C, and D), and MBLs (Ambler Class B) which require divalent cations, usually zinc, as metal cofactors for enzyme activity, thereby facilitating hydrolysis of the bicyclic beta-lactam ring (18).

Thus, according to the invention, in order to increase the expression of Ambler Class B carbapenemase producers, the culture medium comprises a carbapenemase activator, which is selected from the group consisting of divalent cations and mixtures thereof.

Typically, in the case of carbapenemases of Ambler class B, the activator is a divalent cation or salt thereof selected from the group consisting of manganese, cobalt, nickel, cadmium, mercury, zinc and mixtures thereof (see Biochem J. 1974; 143(1):129-35 and the Journal of Biological Chemistry vol. 285, NO. 7, 4570-4577). Preferably, the carbapenemase activator is zinc.

Typically, the concentration of carbapenemase activator which is found in the culture medium is comprised between 10 or 30 and 100 µg/ml, preferably between 50 and 80 µg/ml, and more preferably the concentration of carbapenemase activator is about 70 µg/ml.

According to the invention, the M-type penicillin (also called methicillin type penicillin) is selected from the group consisting of cloxacillin, dicloxacillin, flucloxacillin, oxacillin, methicillin, nafcillin and mixtures thereof. Preferably the M-type penicillin is cloxacillin.

Typically, the concentration of M-type penicillin which is found in the culture medium is comprised between 100 and 500 µg/ml, preferably between 200 and 300 µg/ml, and more preferably the concentration of M-type penicillin is about 250 µg/ml.

Although, the culture medium according to the invention preferably comprises ertapenem, zinc and cloxacillin, any combination of carbapenem, carbapenemase activator and M-type penicillin as disclosed herein may be used in the culture medium of the present invention.

Typically, the culture medium according to the invention is an agar culture medium, wherein the culture medium is, for example, agar-based. Alternatively, the culture medium may be a broth liquid medium.

In addition, to the combination of carbapenem, carbapenemase activator and M-type penicillin, the culture medium according to the invention also comprises nutrients necessary to support the growth, proliferation and survival of the bacteria. Thus, an appropriate culture medium according to the invention typically comprises, in addition to the combination of carbapenem, carbapenemase activator and M-type penicillin, a minimal medium in which bacteria can grow. Typical examples of such minimal media are Drigalski, Trypticase soy and MacConckey.

Preferably the medium is selective for Gram-negative bacteria such as the Drigalski medium. Alternatively, selection of Gram negative bacteria may be based on antibiotic-antifungal drug association using a non-selective media such as Trypticase soy agar. In that case, the medium can comprise an antibiotic specific for gram positive bacteria such as a glycopeptide antibiotic or a lipopeptide antibiotic, such as daptomycin. For example the antibiotic can be a glycopeptide antibiotic selected from the group consisting of vancomycin, teicoplanin, telavancin, ramoplanin, and decaplanin. Typically the medium can comprise an antifungal drug, such as a polyene antifungal drug, for example amphotericin B.

Typically, the culture according to the invention may comprise a chromogenic component. A chromogenic component may facilitate species recognition. Suitable chromogenic components are well known and are used for example in the KPC Chromagar or ChromID ESBL or CRE screening media Method of Detection:

According to another aspect of the invention, there is provided a method for detecting carbapenem-resistant bacteria in a test sample comprising the following successive steps:

a) inoculating a culture medium as defined herein with said test sample, b) incubating said culture medium under conditions suitable for growth of carbapenem-resistant bacteria, c) detecting colonies formed on said culture medium corresponding to carbapenem-resistant bacteria.

Typically, once colonies have been detected on the culture medium, further techniques may be used to characterize the beta-lactamase content. Currently, there exist various methods for detecting carbapenemase producers. First, phenotypic-based techniques for in vivo production of carbapenemase such as the "Etest®" and the "Hodge-Test" can be used. Alternatively, molecular detection techniques for carbapenemase genes may be used. Finally, beta-lactamase identification using chromogenic molecules, biochemical, iodometric tests and acidimetric tests can be used as well as molecular techniques for identification of corresponding genes.

According to the present invention, the method may be used to detect carbapenem-resistant bacteria, in particular carbapenemase-producing bacteria, involved in nosocomial and community-acquired infections.

Typically, the carbapenem-resistant bacteria and in particular the carbapenemase-producing bacteria which are detected by the method of the invention have a reduced susceptibility to carbapenems. As used herein, "reduced susceptibility" means decreased susceptibility as compared to wild-type carbapenem susceptibility.

Typically, the carbapenem-resistant bacteria are bacteria, such as carbapenemase-producing bacteria, containing a gene coding for a beta-lactamase of the Ambler class A, B and/or D.

Preferably, the carbapenem-resistant bacteria are selected from the *Enterobacteriaceae* family and more preferably from the genera consisting of *Citrobacter, Enterobacter, Escherichia, Klebsiella* and *Providencia*.

In an embodiment of the invention, the method disclosed herein can be applied directly to a raw test sample comprising a mixture of bacteria without having to isolate the various bacterial strains present in the test sample.

The incubation conditions allowing the growth of carbapenem-resistant bacteria are well-known to the person skilled in the art and are not different from the usual methods.

Since ertapenem shows very good or good stability in an agar medium (2 to 4 weeks), a detection method like the one of the present invention can be carried out effectively over several months.

The invention will further be illustrated in view of the following examples.

EXAMPLES

Example 1

Evaluation of the ETP-Cloxa-Zinc Agar Culture Medium

Applicant evaluated an in-house prepared ertapenem-cloxacillin-zinc (hereinafter, referred to as SUPERCARBA medium) containing agar as an alternative to CHROMagar KPC and ChromID ESBL.

Ertapenem was added at a low concentration of 0.25 µg/ml, $ZnSO_4$ (70 µg/ml) was added to improve growth of metallo-beta-lactamase (MBL)-producers (3) and cloxacillin (250 µg/ml) was used to prevent growth of isolates expressing cephalosporinases with broadened substrate activity, such as *Enterobacter cloacae, Enterobacter aerogenes*, and *Serratia marcescens*.

Forty-seven carbapenemase-producing isolates belonging to various enterobacterial species of worldwide origin were included in the study. These strains had been previously characterized for beta-lactamase content at the molecular level. The strains were as follows:
  KPC-producers (n=4),
  VIM/IMP-producers (n=5),
  NDM-1-producers (n=16),
  OXA-48 producers (n=19),
  OXA-181-producers (n=3).
Twenty-nine out of forty-five carbapenemase producers co-expressed an ESBL (Table 1).

Strains that did not express any carbapenemase were used as control. These control strains were:
  ertapenem susceptible isolates producing an ESBL (n=6, identified as "b" in Table 1),
  ertapenem susceptible isolates producing a high-level AmpC (n=5, identified as "c" in Table 1),
  isolates with reduced susceptibility to ertapenem due to over-expressed AmpC (n=4, identified as "d" in Table 1),
  isolates with reduced susceptibility to ertapenem due to ESBL and/or porin deficiency (n=12, identified as "e" in Table 1).

Using an inoculum of ~$2×10^7$ CFU/ml (range, $1.5×10^7$ to $3.5×10^8$ CFU/ml), serial 10-fold dilutions of the isolates were made in normal saline and 100 µl were plated onto SUPERCARBA containing Drigalski agar. Viable bacteria were counted after 24 hours of culture at 37° C. and growth on selective SUPERCARBA media was compared to growth on Drigalski agar without SUPERCARBA.

The lowest limit of detection of VIM and IMP producers ranged from $1×10^1$ to $1×10^6$ CFU/ml (Table 1). Although addition of zinc sulfate helped to lower this detection limit for VIM-producers, IMP-producing isolates which were not always efficiently detected on this medium.

The lowest limit of detection of OXA-48, OXA-181, NDM-1 and KPC producers was $1×10^1$ to $1×10^2$ CFU/ml (Table 1). This result is, to the Applicant's knowledge, one of the most efficient ways to detect carbapenemase-producing isolates. Only one isolate (NDM-1 producing *P. stuartii* isolate) was not efficiently detected on this SUPERCARBA medium (Table 1). Low level of detection of this isolate might be explained by the low MIC of ertapenem (0.38 µg/ml) and weak expression of NDM-1.

As expected, OXA-181-producing *K. pneumoniae* were efficiently detected on SUPERCARBA. Surprisingly however, a very weak detection was obtained for the OXA-181-producing *Providencia rettgeri* despite high MICs of carbapenems (Table 1). With respect to *P. rettgeri*, contribution of AmpC cephalosporinases and impermeability to many β-lactam molecules may be very important compared to that of carbapenemases for providing the in vivo observer level of carbapenem resistance.

As expected, isolates that did not express any carbapenemase (i.e. AmpC and/or ESBL positive isolates) were inhibited on SUPERCARBA (with a detection limit of >$10^7$ CFU/ml). In particular, cloxacillin helped to prevent growth of isolates expressing cephalosporinases with broadened substrate activity (Table 1). Nevertheless, among 12 ertapenem non-susceptible isolates (one *C. freundii* and eleven *K. pneumoniae* isolates) for which porin loss was very likely involved in ertapenem resistance, 50% (n=6) were detected on SUPERCARBA (lower detection limit <$10^2$ CFU/ml) (Table 1, species identified with "e").

Addition of zinc sulfate was useful for eliminating part (up to 42%, n=5) of non-carbapenemase producing ertapenem-resistant *K. pneumoniae* isolates (19, 20, 21). Further studies are needed to investigate the effect of zinc on the outer-membrane protein profile of *K. pneumoniae*.

TABLE 1

Sensitivity of detection of SUPERCARBA medium for 45 carbapenemase- and/or ESBL/AmpC-producing enterobacterial isolates.

| Strains | Beta-lactamases | MIC (µg/ml) of drug[a]: | | | Lowest Detection limit (CFU/ml) |
|---|---|---|---|---|---|
| | | IPM | ETP | MEM | |
| | OXA-48 | | | | |
| K. pneumoniae BIC | OXA-48 | 0.5 | 2 | 0.5 | $1 \times 10^1$ |
| K. pneumoniae CHA | OXA-48 + TEM-1 | 0.38 | 1 | 0.5 | $1 \times 10^1$ |
| K. pneumoniae EGY | OXA-48 + CTX-M-15 | 2 | 3 | 2 | $1 \times 10^1$ |
| K. pneumoniae BEL | OXA-48 | 1 | 4 | 1 | $1 \times 10^1$ |
| K. pneumoniae RAM | OXA-48 | 1 | 4 | 1 | $1 \times 10^1$ |
| K. pneumoniae LIB | OXA-48 | >32 | >32 | >32 | $1 \times 10^1$ |
| K. pneumoniae BEY | OXA-48 + CTX-M-15 + TEM-1 | 0.38 | 0.38 | 0.38 | $1 \times 10^1$-$1 \times 10^2$ |
| K. pneumoniae DAL | OXA-48 + CTX-M-15 + TEM-1 | 0.38 | 2 | 0.38 | $1 \times 10^1$ |
| K. pneumoniae ROB | OXA-48 + CTX-M-15 + TEM-1 | 0.38 | 3 | 0.5 | $1 \times 10^1$ |
| K. pneumoniae SCO | OXA-48 | 0.5 | 0.75 | 0.25 | $1 \times 10^1$ |
| E. cloacae TUR | OXA-48 + SHV-5 | 0.5 | 0.5 | 0.5 | $1 \times 10^1$ |
| E. coli BER | OXA-48 + CTX-M-15 | 0.38 | 1.5 | 0.19 | $1 \times 10^1$ |
| E. coli AME | OXA-48 + CTX-M-24 | 0.25 | 0.5 | 0.19 | $1 \times 10^1$ |
| E. coli GOG | OXA-48 + CTX-M-24 | 0.5 | 1.5 | 0.25 | $1 \times 10^1$ |
| E. coli NAA | OXA-48 + CTX-M-24 | 0.5 | 2 | 0.25 | $1 \times 10^1$ |
| E. coli HAN | OXA-48 + CTX-M-15 | 3 | 16 | 1 | $1 \times 10^1$-$1 \times 10^2$ |
| E. coli BOU | OXA-48 + CTX-M-15 | 0.5 | 0.75 | 0.125 | $1 \times 10^1$-$1 \times 10^2$ |
| E. coli BON | OXA-48 + CTX-M-24 + TEM-1 | 0.38 | 0.5 | 0.19 | $1 \times 10^2$ |
| E. coli BOK | OXA-48 + CTX-M-15 | 0.25 | 0.38 | 0.19 | $1 \times 10^2$ |
| | OXA-181 | | | | |
| K. pneumoniae OMA | OXA-181 + CTX-M-15 + OXA-1 | 0.5 | 2 | 0.5 | $1 \times 10^1$ |
| K. pneumoniae HOL | OXA-181 + CTX-M-15 | 1 | 4 | 1 | $1 \times 10^1$ |
| P. rettgeri RAP | OXA-181 + OXA-1 | 8 | 1 | 2 | $5 \times 10^2$ |
| | NDM-1 | | | | |
| K. pneumoniae UK | NDM-1 + CTX-M-15 + CMY-4 + OXA-1 | >32 | >32 | >32 | $1 \times 10^1$ |
| K. pneumoniae 6642 GEN | NDM-1 + CTX-M-15 + OXA-1 + OXA-10 | 1 | 16 | 3 | $1 \times 10^1$ |
| K. pneumoniae 6759 GEN | NDM-1 + CTX-M-15 + OXA-1 + OXA-9 + OXA-10 + CMY16 | 12 | >32 | >32 | $1 \times 10^1$ |
| K. pneumoniae 1 OMA | NDM-1 + CTX-M-15 + OXA-1 + OXA-9 | >32 | >32 | >32 | $1 \times 10^1$ |
| K. pneumoniae 2 OLA | NDM-1 + OXA-1 | 1.5 | 6 | 2 | $1 \times 10^1$ |
| K. pneumoniae 7 AFR | NDM-1 + OXA-1 + CTX-M-15 + CMY-6 + TEM-1 | >32 | >32 | >32 | $1 \times 10^1$ |
| K. pneumoniae IND | NDM-1 + OXA-1 + CTX-M-15 | 1 | 8 | 4 | $1 \times 10^1$ |
| E. coli GEN | NDM-1 + OXA-1 + CMY-30 + TEM-1 | 8 | >32 | 12 | $1 \times 10^1$ |
| E. coli RIC | NDM-1 + OXA-1 + OXA-10 + CMY-16 | 1 | 3 | 1 | $1 \times 10^1$ |
| E. coli GUE | NDM-1 + OXA-1 + TEM-1 | 3 | 3 | 2 | $1 \times 10^1$ |
| E. coli AUS | NDM-1 + CTX-M-15 + TEM-1 | 6 | 32 | 16 | $1 \times 10^1$ |
| E. coli ALL | NDM-1 + OXA-1 + OXA-2 + CTX-M-15 + TEM-1 | 4 | >32 | 8 | $1 \times 10^1$ |
| E. coli IR5 | NDM-1 + CTX-M-15 + TEM-1 | 16 | >32 | 16 | $1 \times 10^1$ |
| E. cloacae IR38 | NDM-1 + CTX-M-15 | 2 | 16 | 2 | $1 \times 10^1$ |
| P. stuartii NDM | NDM-1 + OXA-1 + CMY-6 | 12 | 0.38 | 1.5 | $>5 \times 10^7$ |
| C. freundii STE | NDM-1 + OXA-1 + OXA-9 + OXA-10 + CTX-M-15 + TEM-1 | >32 | >32 | >32 | $1 \times 10^1$ |
| | KPC-2 | | | | |
| E. coli PSP | KPC-2 | 0.5 | 0.5 | 0.5 | $1 \times 10^2$ |
| E. cloacae | KPC-2 | 4 | 6 | 2 | $1 \times 10^1$ |
| E. coli COL | KPC-2 | 4 | 4 | 2 | $1 \times 10^1$ |
| K. pneumoniae COL | KPC-2 + TEM-1 + SHV-1 + CTX-M-15 | 4 | 4 | 32 | $1 \times 10^1$ |
| | VIM or IMP | | | | |
| E. coli MAD | VIM-1 + CTX-M-3 | 1.5 | 0.38 | 0.5 | $1 \times 10^5$ |
| E. coli DIH | VIM-19 | 8 | 16 | 4 | $1 \times 10^1$ |
| K. pneumoniae MAD | VIM-1 + CTX-M-3 | 1 | 0.5 | 1 | $1 \times 10^1$ |
| E. coli JAP | IMP-1 | 0.5 | 3 | 0.5 | $1 \times 10^6$ |
| K. pneumoniae TUR | IMP-1 | 1 | 2 | 8 | $1 \times 10^6$ |
| | Controls | | | | |
| K. pneumoniae KPN[b] | CTX-M-15 | 0.12 | 0.12 | 0.12 | $>5 \times 10^7$ |
| E. cloacae CLO[b] | CTX-M-15 | 0.12 | 0.12 | 0.12 | $>6 \times 10^7$ |

TABLE 1-continued

Sensitivity of detection of SUPERCARBA medium for 45 carbapenemase- and/or ESBL/AmpC-producing enterobacterial isolates.

| | | MIC (µg/ml) of drug[a]: | | | Lowest Detection limit |
|---|---|---|---|---|---|
| Strains | Beta-lactamases | IPM | ETP | MEM | (CFU/ml) |
| E. coli FOR[b] | CTX-M-15 | 0.12 | 0.12 | 0.12 | $>6 \times 10^7$ |
| E. coli E14[b] | CTX-M-14 | 0.12 | 0.12 | 0.12 | $>4 \times 10^7$ |
| E. cloacae CVB[b] | VEB-1 | 0.12 | 0.12 | 0.12 | $>5 \times 10^7$ |
| E. coli EVB[b] | VEB-1 | 0.12 | 0.12 | 0.12 | $>3 \times 10^7$ |
| P. mirabilis PMA[c] | ACC-1 | 0.25 | 0.12 | 0.12 | $>5 \times 10^7$ |
| E. coli ECA[c] | ACC-1 | 0.12 | 0.12 | 0.12 | $>5 \times 10^7$ |
| K. pneumoniae KDH[c] | DHA-2 | 0.12 | 0.5 | 0.12 | $>5 \times 10^7$ |
| E. coli MET[c] | Chromosome-encoded extended-spectrum cephalosporinase | 0.12 | 0.12 | 0.12 | $>5 \times 10^7$ |
| E. coli SYD[c] | CMY-2 | 0.12 | 0.12 | 0.12 | $>5 \times 10^7$ |
| E. cloacae ARF[d] | AmpC | 0.12 | 1 | 0.12 | $>5 \times 10^7$ |
| E. cloacae BLA[d] | AmpC | 0.12 | 1 | 0.12 | $>5 \times 10^7$ |
| E. cloacae CON[d] | AmpC | 0.12 | 1 | 0.12 | $>5 \times 10^7$ |
| E. cloacae AZA[d] | AmpC | 0.12 | 1 | 0.12 | $>5 \times 10^7$ |
| K. pneumoniae MEK[e] | CTX-M-15 + SHV-11 | 1.5 | >32 | 6 | $1 \times 10^1$ |
| K. pneumoniae SIM[e] | CTX-M-15 + TEM-1 + SHV-1 | 8 | >32 | 6 | $1 \times 10^1$ |
| K. pneumoniae SHM[e] | CTX-M-15 + TEM-1 + SHV-11 | 3 | >32 | 1 | $1 \times 10^1$ |
| K. pneumoniae COO[e] | CTX-M-15 + SHV28 | 8 | >32 | 4 | $1 \times 10^1$ |
| K. pneumoniae FOS[e] | CTX-M-15 + TEM-1 + SHV-11 | 6 | >32 | >32 | $1 \times 10^2$ |
| K. pneumoniae 648236[e] | SHV-2a | 0.25 | 2 | 0.38 | $1 \times 10^2$ |
| K. pneumoniae BER[e] | TEM-1 + SHV-28 | 1 | 4 | 1 | $1 \times 10^3$ |
| K. pneumoniae BED[e] | CTX-M-15 + TEM-1 + SHV-1 | 1.5 | >32 | 4 | $1 \times 10^4$ |
| K. pneumoniae SHI[e] | CTX-M-15 + TEM-1 + SHV-1 | 0.25 | 1 | 1 | $7 \times 10^4$ |
| K. pneumoniae LEG[e] | CTX-M-15 + TEM-1 + SHV-12 | 0.75 | >32 | 3 | $2 \times 10^4$ |
| K. pneumoniae ALE[e] | CTX-M-15 + SHV-1 | 1 | >32 | 4 | $1 \times 10^5$ |
| C. freundii MAU[e] | Overexpressed AmpC + TEM-3 | 1 | 8 | 1 | $1 \times 10^5$ |

[a]Abbreviations: IMP, imipenem; ETP, ertapenem; MP, meropenem.
[b]Ertapenem susceptible isolates producing an ESBL.
[c]Ertapenem susceptible isolates producing a high-level AmpC.
[d]Reduced susceptibility to ertapenem due to overexpressed AmpC.
[e]Reduced susceptibility to ertapenem due to porin deficiency.
Beta-lactame of the ESBL type: CTX-M, TEM, SHV, VEB.
Beta lactame of the High-level AmpC type: ACC, DHA, CMY.

The results above show that the Applicant has developed a new, reliable and highly sensitive culture medium for detecting carbapenemase-producing bacteria isolates from a collection of well-characterized strains, and preferably isolates with a reduced susceptibility to carbapenems. Almost all OXA-48, NDM-1 and KPC-type carbapenemase producers were detected with a low detection limit of $1 \times 10^1$ to $1 \times 10^2$ CFU/ml by using this medium. In fact, the specificity and sensitivity of the culture medium according to the invention is much higher than that of the ChromID ESBL and the CHROMagar-KPC media.

Example 2

Storage Stability of the SUPERCARBA Agar Culture Medium

To assess the storage stability of SUPERCARBA agar, E. cloacae ARF with over-expressed AmpC was sub-cultured daily onto plates from a single batch of SUPERCARBA Drigalski agar stored at 4° C. Growth of E. cloacae ARF was consistently inhibited on the SUPERCARBA agar throughout a seven-day period.

Example 3

Detection of Carbapenemase Producers in Enterobacteriaceae using a Novel Screening Medium Abstract A Drigalski agar-based culture medium containing ertapenem, cloxacillin, and zinc sulfate (SUPERCARBA medium) was tested for screening carbapenemase-producing Enterobacteriaceae. OXA-48 (n=44), NDM (n=25), VIM/IMP (n=27), and KPC producers (n=18) were detected with a low detection limit. Its overall sensitivity (95.6%) was higher than those of the currently available ChromID ESBL (bioMerieux) and the CHROMagar-KPC(CHROMagar) screening media. The SUPERCARBA medium provides a significative improvement for detection of the most common types of carbapenemase producers.

Taking into account the current importance of detecting carbapenemase producers with accuracy, we have designed a novel screening (termed SUPERCARBA) medium. The rationale for the design of this medium was that it should be able to detect carbapenemase producers with low-level resistance to carbapenems, and be as selective as possible by inhibiting growth of carbapenem-resistant but non-carbapenemase producing isolates.

Different concentrations of several carbapenem molecules were tested, and finally ertapenem was added to a Drigalski agar medium at a concentration of 0.25 µg/ml. $ZnSO_4$ (70 µg/ml) was added to improve expression of metallo-β-lactamases by MBL producers. Cloxacillin (250 µg/ml) which is a cephalosporinase (AmpC-type β-lactamase) inhibitor was used to prevent growth of isolates expressing high level expression of cephalosporinases, such as *Enterobacter cloacae, Enterobacter aerogenes, Morganella morgannii,* and *Serratia marcescens.* Those isolates are clinically-significant sources of carbapenem resistance when outer-membrane permeability defect is associated (Girlich, et al., 2009. Antimicrob. Agents Chemother. 53:832-834, Mammeri et al. 2008. FEMS Microbiol. Lett. 282:238-240).

One-hundred and fourteen carbapenemase-producing isolates belonging to various enterobacterial species of worldwide origin were included in the study, all having a β-lactamase content characterized at the molecular level (Table 2). The strains were as follows: KPC producers (n=18), VIM producers (n=12), IMP producers (n=15), NDM-1 producers (n=25), together with OXA-48-(n=41) and OXA-181 producers (n=3). Seventy-five of those isolates co-expressed an ESBL (Table 2). Strains that did not express any carbapenemase were used as controls, consisting in isolates showing reduced susceptibility to ertapenem due to an overexpressed AmpC (n=10), or to an ESBL (n=12), and/or porin deficiency. Wild-type ertapenem-susceptible isolates, restricted-spectrum β-lactamase producers, ESBL producers, and high-level AmpC producers were also included as controls (n=40) (Table 2). Using an inoculum of ~$2\times10^7$ CFU/ml (range, $1.5\times10^7$ to $3.5\times10^8$ CFU/ml), serial 10-fold dilutions of the isolates were made in normal saline and 100 µl were plated onto the SUPERCARBA medium and compared to results obtained using CHROMagar KPC and ChromID ESBL. Viable bacteria were counted after 24 h of culture at 37° C. The sensitivity and specificity cut-off values were set at $1\times10^3$ CFU/ml, i-e. a limit value of $1\times10^3$ CFU/ml and above was considered as "not efficiently detected".

The lowest limit of detection of OXA-48, OXA-181, NDM-1 and KPC producers ranged from $1\times10^1$ to $1\times10^2$ CFU/ml (Table 2). A single NDM producer (NDM-1-producing *Providencia stuartii* isolate (Poirel et al., 2011. Antimicrob. Agents Chemother. 55:5403-5407.) was not efficiently detected on the SUPERCARBA medium (limit of detection $1\times10^7$ CFU/ml) (Table 2). Its lack of detection might be explained by its low MIC values of ertapenem (0.38 µg/ml) and a likely weak expression of the $bla_{NDM-1}$ gene, related to chromosomal insertion of the $bla_{NDM-1}$ gene. As expected, OXA-181-producing *K. pneumoniae* were also well detected with the SUPERCARBA medium. The lowest limit of detection of VIM and IMP producers ranged from $1\times10^1$ to $1\times10^6$ CFU/ml (Table 1). Although addition of zinc sulfate decreased significantly to lower the detection limit for VIM and IMP producers, a few VIM and IMP producers were not efficiently detected on this medium (detection limit $>1\times10^3$ CFU/ml). As expected, growth of isolates that do not express any carbapenemase (i.e. AmpC and/or ESBL producers) was inhibited by the SUPERCARBA medium (with a detection limit much higher than $1\times10^3$ CFU/ml). In particular, cloxacillin addition prevented growth of the isolates expressing cephalosporinases (Table 2). As previously shown, porin defect resulting in a decreased outer-membrane permeability leads to a reduced susceptibility to ertapenem of *E. coli* and *K. pneumoniae*. In this study, among the 19 ertapenem non-susceptible isolates, with MIC values of ertapenem being >0.25 µg/ml (1 *Citrobacter freundii,* 2 *E. coli,* 4 *E. cloacae,* and 12 *K. pneumoniae* isolates) and for which porin defect was involved in ertapenem resistance, 58% (n=11) were detected by selection on the SUPERCARBA medium (lower detection limit <$10^2$ CFU/ml) (Table 2). Addition of zinc sulfate and cloxacillin was useful for prevention of growth of many (up to 42%, n=8) of non-carbapenemase producing carbapenem-resistant isolates. Noticeably, non-carbapenemase-producing *Acinetobacter baumannii* and *Pseudomonas aeruginosa,* grew on the SUPERCARBA medium (data not shown). Similar results of growth of non-enterobacterial Gram negative rods were obtained using the ChromID ESBL and the CHROMagar KPC media (data not shown). These three media are suitable only for selection of *Enterobacteriaceae.*

A comparison of the results obtained with the ChromID ESBL and CHROMagar KPC media with those obtained with the SUPERCARBA medium showed that this latter screening medium is more efficient to detect carbapenemase-producing isolates (Tables 2 and 3). Indeed, sensitivity of the SUPERCARBA medium was 95.6%, higher than that of the ChromID ESBL (87.7%), and of the CHROMagar KPC (40.3%) medium. Moreover, the sensitivities of SUPERCARBA, determined for each class of carbapenemase producers, was higher (100%, 90% and 100% for classes A, B, and D, respectively) than those obtained for the two other screening media (Table 3). The specificity of the SUPERCARBA medium was also high (82.2%). A further improvement of the SUPERCARBA medium would be the addition of chromogenic molecules that would permit a species recognition.

To assess the storage ability of the SUPERCARBA medium, *E. cloacae* ARF that over-expressed AmpC was subcultured daily onto Drigalski plates from a single batch of SUPERCARBA medium stored at 4° C. Growth of this isolate was consistently inhibited on the SUPERCARBA agar during a seven-day period.

We propose here the very first screening medium that may detect not only KPC-, MBL-, but also OXA-48-producers. This medium represents a significative improvement as compared to the available screening media to detect carbapenemase producers, and particularly for detection of OXA-48 producers that do not co-express any ESBL. Taking into account that SUPERCARBA medium contains ertapenem at a low concentration, it may detect carbapenemase producers with low level resistance to carbapenems, which is a situation frequently observed for OXA-48 producers. In addition, this medium is useful for selecting specifically carbapenemase producers in stools that contain also a large amount of ESBL producers which growth will be inhibited. This property is particularly relevant, since high rates of ESBL carriage is now reported worldwide.

Modified SUPERCARBA media were prepared with similar results (see tables 4 to 11).

TABLE 2

Limit of detection of SUPERCARBA medium for 176 carbapenemase- and/or ESBL/AmpC-producing enterobacterial isolates as compared to those obtained with ChromID ESBL and CHROMagar KPC media. MIC values of imipenem, ertapenem and meropenem are provided for each strain.

| Strains | -Lactamase content | MIC (µg/ml) | | | Lowest detection limit (CFU/ml) | | |
|---|---|---|---|---|---|---|---|
| | | IPM[a] | ETP | MEM | SUPERCARBA | ChromID ESBL | CHROMagar KPC |
| Ambler class A carbapenemases (KPC) | | | | | | | |
| K. pneumoniae 2303 | KPC-2[b] + SHV-11 | >32 | >32 | >32 | $1 \times 10^1$ | $1 \times 10^1$ | $1 \times 10^1$ |
| K. pneumoniae LIE | KPC-2 + TEM-2 + OXA-9 | >32 | >32 | >32 | $5 \times 10^1$ | $1 \times 10^1$ | $1 \times 10^1$ |
| K. pneumoniae GES | KPC-2 + TEM-1 + SHV-11 | 6 | 12 | 1.5 | $1 \times 10^1$ | $1 \times 10^1$ | $\overline{1 \times 10^{3\,c}}\,/\,1 \times 10^1$ |
| K. pneumoniae 588 | KPC-2 + TEM-1 + SHV-11 + OXA-9 | 24 | 32 | 16 | $1 \times 10^1$ | $1 \times 10^1$ | $1 \times 10^1$ |
| K. pneumoniae YC | KPC-2 + TEM-1 + SHV-11 + SHV-12 + OXA-9 | 4 | 24 | 2 | $1 \times 10^1$ | $1 \times 10^1$ | $1 \times 10^1$ |
| K. pneumoniae A28006 | KPC-2 + TEM-1 + CTX-M-2 + SHV-11 | 16 | 24 | 32 | $2 \times 10^1$ | $1 \times 10^1$ | $1 \times 10^1$ |
| K. pneumoniae A33504 | KPC-2 + TEM-1 + SHV-11 + CTX-M-2 + OXA-9 | >32 | >32 | >32 | $1 \times 10^1$ | $1 \times 10^1$ | $1 \times 10^1$ |
| K. pneumoniae MUS | KPC-2 + TEM-1 + SHV-11 + SHV-12 | 0.75 | 4 | 1.5 | $1 \times 10^1$ | $1 \times 10^1$ | $\overline{1 \times 10^3}$ |
| K. pneumoniae KAM | KPC-3 + TEM-1 + SHV-11 | 8 | 12 | 2 | $1 \times 10^1$ | $1 \times 10^1$ | $\overline{5 \times 10^3}$ |
| E. coli PSP | KPC-2 + TEM-1 + OXA-1 | 0.5 | 0.5 | 0.5 | $1 \times 10^2$ | $1 \times 10^1$ | $\overline{1 \times 10^4}\,/\,1 \times 10^1$ |
| E. coli DIN | KPC-2 + TEM-1 + OXA-1 | 1 | >32 | 0.5 | $1 \times 10^1$ | $1 \times 10^1$ | $1 \times 10^1$ |
| E. coli COL | KPC-2 + TEM-1 + CTX-M-9 | 4 | 4 | 2 | $1 \times 10^1$ | $1 \times 10^1$ | $\overline{1 \times 10^3}\,/\,1 \times 10^1$ |
| E. coli LIL | KPC-2 + TEM-1 + OXA-9 | 2 | 1.5 | 1 | $1 \times 10^1$ | $1 \times 10^1$ | $1 \times 10^1$ |
| E. cloacae HMG | KPC-2 + TEM-1 | 24 | >32 | 16 | $1 \times 10^2$ | $1 \times 10^1$ | $1 \times 10^1$ |
| E. cloacae CFVL | KPC-2 + TEM-3 | 4 | 2 | 1 | $1 \times 10^1$ | $1 \times 10^1$ | $\overline{5 \times 10^5}$ |
| E. cloacae HPTU | KPC-2 + TEM-1 + SHV-11 | 2 | 4 | 1.5 | $1 \times 10^1$ | $1 \times 10^1$ | $\overline{1 \times 10^1}$ |
| S. marcescens D6403 | KPC-2 + TEM-1 | >32 | >32 | >32 | $1 \times 10^1$ | $1 \times 10^1$ | $1 \times 10^1$ |
| S. marcescens C7052 | KPC-2 + TEM-1 + SHV-12 | >32 | >32 | >32 | $1 \times 10^1$ | $1 \times 10^1$ | $1 \times 10^1$ |
| Ambler class B carbapenemases | | | | | | | |
| K. pneumoniae OMA419 | NDM-1 + OXA-1 | 1.5 | 6 | 2 | $1 \times 10^1$ | $1 \times 10^1$ | $1 \times 10^2$ |
| K. pneumoniae KI2 | NDM-1 + CTX-M-15 + OXA-1 | 1 | 8 | 4 | $1 \times 10^1$ | $1 \times 10^1$ | $1 \times 10^1$ |
| K. pneumoniae UK | NDM-1 + CTX-M-15 + CMY-4 + OXA-1 | >32 | >32 | >32 | $1 \times 10^1$ | $1 \times 10^1$ | $1 \times 10^1$ |
| K. pneumoniae 6642 GEN | NDM-1 + CTX-M-15 + OXA-1 + OXA-10 | 1 | 16 | 3 | $1 \times 10^1$ | $1 \times 10^1$ | $1 \times 10^1$ |
| K. pneumoniae 6759 GEN | NDM-1 + CTX-M-15 + CMY-16 + OXA-1 + OXA-9 + OXA-10 | 12 | >32 | >32 | $1 \times 10^1$ | $1 \times 10^1$ | $1 \times 10^1$ |
| K. pneumoniae OMA601 | NDM-1 + CTX-M-15 + OXA-1 + OXA-9 | >32 | >32 | >32 | $1 \times 10^1$ | $1 \times 10^1$ | $1 \times 10^1$ |
| K. pneumoniae 7AFR | NDM-1 + TEM-1 + CTX-M-15 + CMY-6 + OXA-1 | >32 | >32 | >32 | $1 \times 10^1$ | $1 \times 10^1$ | $1 \times 10^1$ |
| K. pneumoniae OM2 | NDM-1 + TEM-1 + CTX-M-3 + SHV-11 + OXA-1 | 0.75 | 8 | 1.5 | $1 \times 10^1$ | $1 \times 10^1$ | $\overline{3 \times 10^4}$ |
| K. pneumoniae OM4 | NDM-1 + TEM-1 + CTX-M-15 + SHV-12 + OXA-9 | 4 | >32 | 16 | $1 \times 10^1$ | $1 \times 10^1$ | $1 \times 10^1$ |
| K. pneumoniae OM8 | NDM-1 + TEM-1 + CTX-M-15 + SHV-11 + OXA-1 | 2 | >32 | 4 | $2 \times 10^1$ | $1 \times 10^1$ | $1 \times 10^2$ |
| K. pneumoniae OM13 | NDM-1 + TEM-1 + CTX-M-15 + SHV-28 + OXA-1 + OXA-9 | 3 | 4 | 2 | $1 \times 10^1$ | $1 \times 10^1$ | $\overline{3 \times 10^4}$ |
| K. pneumoniae OM15 | NDM-1 + CTX-M-15 + SHV-130 + OXA-1 | 1.5 | 12 | 3 | $1 \times 10^1$ | $1 \times 10^1$ | $\overline{3 \times 10^5}$ |
| K. pneumoniae OM16 | NDM-1 + CTX-M-15 + OXA-1 + OXA-181 | 8 | >32 | 16 | $3 \times 10^1$ | $1 \times 10^1$ | $\overline{1 \times 10^1}$ |
| K. pneumoniae OM19 | NDM-1 + CTX-M-15 + SHV-12 + OXA-1 | 4 | 24 | 8 | $1 \times 10^1$ | $1 \times 10^1$ | $4 \times 10^2$ |
| K. pneumoniae KIE | NDM-1 + SHV-38 + CMY-6 + OXA-10 | 0.75 | 2 | 1 | $1 \times 10^1$ | $1 \times 10^1$ | $\overline{1 \times 10^4}$ |
| E. coli GUE | NDM-1 + TEM-1 + OXA-1 | 3 | 3 | 2 | $1 \times 10^1$ | $1 \times 10^1$ | $\overline{1 \times 10^5}\,/\,1 \times 10^1$ |
| E. coli AUS | NDM-1 + TEM-1 + CTX-M-15 | 6 | 32 | 16 | $1 \times 10^1$ | $1 \times 10^1$ | $1 \times 10^1$ |
| E. coli IR5 | NDM-1 + TEM-1 + CTX-M-15 | 16 | >32 | 16 | $1 \times 10^1$ | $1 \times 10^1$ | $1 \times 10^1$ |
| E. coli GEN | NDM-1 + TEM-1 + CMY-30 + OXA-1 | 8 | >32 | 12 | $1 \times 10^1$ | $1 \times 10^1$ | $1 \times 10^1$ |
| E. coli RIC | NDM-1 + CMY-16 + OXA-1 + OXA-10 | 1 | 3 | 1 | $1 \times 10^1$ | $1 \times 10^1$ | $\overline{1 \times 10^5}\,/\,1 \times 10^1$ |
| E. coli ALL | NDM-1 + TEM-1 + CTX-M-15 + OXA-1 + OXA-2 | 4 | >32 | 8 | $1 \times 10^1$ | $1 \times 10^1$ | $1 \times 10^1$ |
| E. coli OM20 | NDM-1 + TEM-1 + CTX-M-15 | 2 | >32 | 8 | $1 \times 10^1$ | $1 \times 10^1$ | $1 \times 10^1$ |
| E. cloacae IR38 | NDM-1 + CTX-M-15 | 2 | 16 | 2 | $1 \times 10^1$ | $3 \times 10^2$ | $\overline{4 \times 10^4}$ |
| P. stuartii PS1 | NDM-1 + CMY-6 + OXA-1 | 12 | 0.38 | 1.5 | $\overline{1 \times 10^7}\,/\,1 \times 10^1$ | $\overline{1 \times 10^3}\,/\,1 \times 10^1$ | $\overline{1 \times 10^7}\,/\,1 \times 10^1$ |
| C. freundii STE | NDM-1 + TEM-1 + CTX-M-15 + VIM-4 + OXA-1 + OXA-9 + OXA-10 + OXA-181 | >32 | >32 | >32 | | | |
| K. pneumoniae 0404024 | VIM-1 | >32 | >32 | >32 | $1 \times 10^1$ | $1 \times 10^1$ | $1 \times 10^1$ |
| K. pneumoniae 0511135 | VIM-1 + SHV-12 | >32 | >32 | >32 | $1 \times 10^1$ | $1 \times 10^1$ | $1 \times 10^1$ |
| K. pneumoniae 0404020 | VIM-1 + SHV-5 | >32 | >32 | >32 | $1 \times 10^1$ | $1 \times 10^1$ | $1 \times 10^1$ |
| K. pneumoniae ENN | VIM-1 + SHV-5 | 0.5 | 1.5 | 0.38 | $1 \times 10^1$ | $1 \times 10^1$ | $1 \times 10^1$ |
| K. pneumoniae MAD | VIM-1 + CTX-M-3 | 1 | 0.5 | 1 | $1 \times 10^1$ | $1 \times 10^1$ | $\overline{2 \times 10^4}$ |
| E. coli DIH | VIM-19 | 8 | 16 | 4 | $1 \times 10^1$ | $1 \times 10^1$ | $\overline{1 \times 10^1}$ |
| E. coli 0404018 | VIM-1 + CMY-6 | 3 | 1.5 | 1 | $5 \times 10^1$ | $1 \times 10^1$ | $>1 \times 10^8$ |
| E. coli 1008077 | VIM-1 + TEM-1 + CTX-M-15 | >32 | 4 | 4 | $1 \times 10^1$ | $1 \times 10^1$ | $>1 \times 10^8$ |
| E. coli MAD | VIM-1 + CTX-M-3 | 1.5 | 0.38 | 0.5 | $\overline{1 \times 10^5}$ | $1 \times 10^1$ | $\overline{2 \times 10^5}$ |
| E. cloacae KAR | VIM-1 + SHV-70 | 1 | 0.38 | 0.5 | $\overline{1 \times 10^6}$ | $1 \times 10^1$ | $>1 \times 10^8$ |
| E. cloacae 1008029 | VIM-1 + CTX-M-3 | >32 | >32 | >32 | $\overline{2 \times 10^1}$ | $1 \times 10^1$ | $\overline{1 \times 10^1}$ |

TABLE 2-continued

Limit of detection of SUPERCARBA medium for 176 carbapenemase- and/or ESBL/AmpC-producing enterobacterial isolates as compared to those obtained with ChromID ESBL and CHROMagar KPC media. MIC values of imipenem, ertapenem and meropenem are provided for each strain.

| | | MIC (µg/ml) | | | Lowest detection limit (CFU/ml) | | |
|---|---|---|---|---|---|---|---|
| Strains | β-Lactamase content | IPM$^a$ | ETP | MEM | SUPERCARBA | ChromID ESBL | CHROMagar KPC |
| S. marcescens 1008091 | VIM-1 + CTX-M-15 | >32 | >32 | >32 | $1 \times 10^1$ | $1 \times 10^1$ | $1 \times 10^1$ |
| K. pneumoniae TUR | IMP-1 | 1 | 2 | 8 | $1 \times 10^6$ | $2 \times 10^1$ | $1 \times 10^1$ |
| K. pneumoniae 0709121 | IMP-1 | 1.5 | 3 | 1 | $1 \times 10^1$ | $1 \times 10^1$ | $1 \times 10^3$ |
| K. pneumoniae 0709124 | IMP-1 + TEM-15 | 8 | 3 | 2 | $1 \times 10^1$ | $1 \times 10^1$ | $1 \times 10^4$ |
| K. pneumoniae 0709125 | IMP-1 + TEM-1 + SHV-12 | 1.5 | 4 | 2 | $1 \times 10^1$ | $1 \times 10^1$ | $1 \times 10^3$ |
| K. pneumoniae 0709127 | IMP-1 + TEM-1 | 0.5 | 4 | 1 | $1 \times 10^1$ | $1 \times 10^1$ | $1 \times 10^4$ |
| K. pneumoniae TWA | IMP-8 | 1 | 1 | 0.5 | $1 \times 10^1$ | $1 \times 10^1$ | $\geq 1 \times 10^8$ |
| K. pneumoniae TAW | IMP-8 + SHV-12 | 0.5 | 0.5 | 0.5 | $4 \times 10^2$ | $1 \times 10^1$ | $\geq 1 \times 10^8$ |
| E. coli JAP | IMP-1 | 0.5 | 3 | 0.5 | $1 \times 10^4$ | $1 \times 10^1$ | $2 \times 10^5$ |
| E. coli TWA | IMP-8 + SHV-12 | 6 | 8 | 3 | $1 \times 10^1$ | $1 \times 10^1$ | $1 \times 10^1$ |
| E. coli 1108013 | IMP-1 + TEM-1 | 0.5 | 4 | 1 | $1 \times 10^1$ | $1 \times 10^1$ | $1 \times 10^6$ |
| E. cloacae TWA | IMP-8 | 1.5 | 1 | 1 | $1 \times 10^1$ | $1 \times 10^1$ | $1 \times 10^2$ |
| E. cloacae TAW | IMP-8 + SHV-12 | 0.75 | 0.5 | 0.5 | $1 \times 10^2$ | $1 \times 10^1$ | $\geq 1 \times 10^8$ |
| E. cloacae 1008079 | IMP-1 | 8 | >32 | >32 | $1 \times 10^1$ | $1 \times 10^2$ | $1 \times 10^7$ |
| E. cloacae 1008187 | IMP-1 + CTX-M-15 | 8 | >32 | 4 | $1 \times 10^1$ | $1 \times 10^2$ | $1 \times 10^4$ |
| S. marcescens 0911033 | IMP-1 | >32 | >32 | >32 | $1 \times 10^1$ | $1 \times 10^1$ | $1 \times 10^1$ |
| Ambler Class D Carbapenemases | | | | | | | |
| K. pneumoniae BIC | OXA-48 | 0.5 | 2 | 0.5 | $1 \times 10^1$ | $\geq 1 \times 10^8$ | $5 \times 10^6$ |
| K. pneumoniae BEL | OXA-48 | 1 | 4 | 1 | $1 \times 10^1$ | $\geq 1 \times 10^8$ | $1 \times 10^6$ |
| K. pneumoniae RAM | OXA-48 | 1 | 4 | 1 | $1 \times 10^1$ | $\geq 1 \times 10^8$ | $1 \times 10^5$ |
| K. pneumoniae LIB | OXA-48 | 16 | 16 | 16 | $1 \times 10^1$ | $\geq 1 \times 10^8$ | $5 \times 10^4$ |
| K. pneumoniae BOU | OXA-48 | 0.38 | 0.5 | 0.25 | $1 \times 10^1$ | $\geq 1 \times 10^8$ | $1 \times 10^8$ |
| K. pneumoniae SCO | OXA-48 | 0.5 | 0.75 | 0.25 | $1 \times 10^1$ | $\geq 1 \times 10^8$ | $\geq 1 \times 10^8$ |
| K. pneumoniae LOU | OXA-48 | 4 | 16 | 0.5 | $1 \times 10^1$ | $\geq 1 \times 10^8$ | $\geq 1 \times 10^8$ |
| K. pneumoniae TIK | OXA-48 | 0.75 | 2 | 0.38 | $1 \times 10^1$ | $\geq 1 \times 10^8$ | $\geq 1 \times 10^8$ |
| K. pneumoniae OM14 | OXA-48 + TEM-1 | 0.5 | 1 | 0.38 | $1 \times 10^1$ | $\geq 1 \times 10^8$ | $5 \times 10^7$ |
| K. pneumoniae CHA | OXA-48 + TEM-1 | 0.38 | 1 | 0.5 | $1 \times 10^1$ | $\geq 1 \times 10^8$ | $\geq 1 \times 10^8$ |
| K. pneumoniae EGY | OXA-48 + CTX-M-15 | 2 | 3 | 2 | $1 \times 10^1$ | $2 \times 10^1$ | $1 \times 10^5$ |
| K. pneumoniae ROU | OXA-48 + CTX-M-15 | 0.5 | 1.5 | 0.25 | $1 \times 10^1$ | $1 \times 10^1$ | $\geq 1 \times 10^8$ |
| K. pneumoniae BEY | OXA-48 + TEM-1 + CTX-M-15 | 0.38 | 0.38 | 0.38 | $5 \times 10^2$ | $1 \times 10^1$ | $1 \times 10^8$ |
| K. pneumoniae DAL | OXA-48 + TEM-1 + CTX-M-15 | 0.38 | 2 | 0.38 | $1 \times 10^1$ | $1 \times 10^1$ | $4 \times 10^5$ |
| K. pneumoniae BAJ | OXA-48 + TEM-1 + CTX-M-15 + SHV-28 | 0.5 | 1.5 | 0.38 | $1 \times 10^1$ | $1 \times 10^1$ | $\geq 1 \times 10^8$ |
| K. pneumoniae BEN | OXA-48 + TEM-1 + CTX-M-15 + SHV-28 | 0.38 | 1 | 0.25 | $1 \times 10^1$ | $1 \times 10^1$ | $\geq 1 \times 10^8$ |
| K. pneumoniae DUW | OXA-48 + TEM-1 + CTX-M-15 + SHV-28 | 32 | 32 | 32 | $1 \times 10^1$ | $1 \times 10^1$ | $1 \times 10^1$ |
| K. pneumoniae SIC | OXA-48 + CTX-M-15 + SHV-28 | 0.25 | 1 | 0.25 | $1 \times 10^1$ | $1 \times 10^1$ | $\geq 1 \times 10^8$ |
| K. pneumoniae AEL | OXA-48 + CTX-M-15 + SHV-28 + OXA-1 | 0.5 | 6 | 0.38 | $1 \times 10^1$ | $1 \times 10^1$ | $5 \times 10^2$ |
| K. pneumoniae AMS | OXA-48 + TEM-1 + CTX-M-15 + OXA-1 | 0.5 | 2 | 0.38 | $1 \times 10^1$ | $1 \times 10^1$ | $\geq 1 \times 10^8$ |
| K. pneumoniae ELK | OXA-48 + TEM-1 + CTX-M-15 + SHV-11 | 0.5 | 3 | 0.38 | $1 \times 10^1$ | $1 \times 10^1$ | $\geq 1 \times 10^8$ |
| K. pneumoniae VER | OXA-48 + TEM-1 + CTX-M-15 + SHV-11 | 0.38 | 2 | 0.38 | $1 \times 10^1$ | $1 \times 10^1$ | $\geq 1 \times 10^8$ |
| K. pneumoniae VSG | OXA-48 + TEM-1 + CTX-M-15 + OXA-1 | 0.75 | 3 | 0.75 | $1 \times 10^1$ | $1 \times 10^1$ | $\geq 1 \times 10^8$ |
| K. pneumoniae HPA | OXA-48 + TEM-1 + CTX-M-15 + OXA-1 | 1.5 | >32 | 12 | $1 \times 10^1$ | $1 \times 10^1$ | $\geq 1 \times 10^8$ |
| K. pneumoniae OM11 | OXA-48 + TEM-1 + CTX-M-14 | 0.5 | 0.75 | 0.25 | $1 \times 10^1$ | $1 \times 10^1$ | $5 \times 10^7$ |
| K. pneumoniae DIA | OXA-48 + TEM-1b + CTX-M-15 + SHV-11 + OXA-1 | >32 | >32 | >32 | $1 \times 10^1$ | $1 \times 10^1$ | $1 \times 10^1$ |
| E. coli ROB | OXA-48 | 0.5 | 0.75 | 0.25 | $2 \times 10^1$ | $\geq 1 \times 10^8$ | $\geq 1 \times 10^8$ |
| E. coli HAN | OXA-48 + CTX-M-15 | 3 | 16 | 1 | $5 \times 10^1$ | $1 \times 10^1$ | $3 \times 10^4$ |
| E. coli BOU | OXA-48 + CTX-M-15 | 0.5 | 0.75 | 0.125 | $2 \times 10^1$ | $1 \times 10^1$ | $\geq 1 \times 10^8$ |
| E. coli OM3 | OXA-48 + TEM-1 + CTX-M-15 | 0.5 | 1 | 0.38 | $1 \times 10^1$ | $1 \times 10^1$ | $\geq 1 \times 10^8$ |
| E. coli OM22 | OXA-48 + TEM-1 + CTX-M-15 | 0.5 | 1 | 0.25 | $1 \times 10^1$ | $1 \times 10^1$ | $\geq 1 \times 10^8$ |
| E. coli BER | OXA-48 + TEM-1 + CTX-M-15 | 0.38 | 1.5 | 0.19 | $5 \times 10^1$ | $1 \times 10^1$ | $\geq 1 \times 10^8$ |
| E. coli AME | OXA-48 + CTX-M-24 | 0.25 | 0.5 | 0.19 | $2 \times 10^1$ | $1 \times 10^1$ | $\geq 1 \times 10^8$ |
| E. coli ZAN | OXA-48 + TEM-1 + CTX-M-14 | 0.38 | 8 | 0.75 | $1 \times 10^1$ | $1 \times 10^1$ | $\geq 1 \times 10^8$ |
| E. coli BON | OXA-48 + TEM-1 + CTX-M-24 | 0.38 | 0.5 | 0.19 | $1 \times 10^1$ | $1 \times 10^1$ | $\geq 1 \times 10^8$ |
| E. coli BOK | OXA-48 + CTX-M-15 | 0.25 | 0.38 | 0.19 | $2 \times 10^1$ | $1 \times 10^1$ | $\geq 1 \times 10^8$ |
| E. cloacae TUR | OXA-48 + SHV-5 | 0.5 | 0.5 | 0.5 | $1 \times 10^1$ | $2 \times 10^1$ | $1 \times 10^7$ |
| E. cloacae 501 | OXA-48 + TEM-1 + CTX-M-15 | 1 | 16 | 1.5 | $1 \times 10^1$ | $1 \times 10^1$ | $1 \times 10^1$ |
| E. cloacae BEU | OXA-48 + TEM-1 + CTX-M-15 + SHV-12 | 0.5 | 8 | 0.5 | $1 \times 10^1$ | $1 \times 10^1$ | $1 \times 10^4$ |
| C. koseri ROU | OXA-48 | 0.38 | 2 | 0.38 | $1 \times 10^1$ | $\geq 1 \times 10^8$ | $\geq 1 \times 10^8$ |
| C. koseri VER | OXA-48 | 0.75 | 2 | 0.38 | $1 \times 10^1$ | $\geq 1 \times 10^8$ | $\geq 1 \times 10^8$ |
| K. pneumoniae HOL | OXA-181 + CTX-M-15 | 1 | 4 | 1 | $1 \times 10^1$ | $1 \times 10^1$ | $1 \times 10^1$ |
| K. pneumoniae OMA | OXA-181 + CTXM-15 + OXA-1 | 0.5 | 2 | 0.5 | $1 \times 10^1$ | $1 \times 10^1$ | $\geq 1 \times 10^8$ |
| P. rettgeri RAP | OXA-181 + OXA-1 | 8 | 1 | 2 | $5 \times 10^2$ | $1 \times 10^1$ | $1 \times 10^1$ |

TABLE 2-continued

Limit of detection of SUPERCARBA medium for 176 carbapenemase- and/or ESBL/AmpC-producing enterobacterial isolates as compared to those obtained with ChromID ESBL and CHROMagar KPC media. MIC values of imipenem, ertapenem and meropenem are provided for each strain.

| | | MIC (μg/ml) | | | Lowest detection limit (CFU/ml) | | |
|---|---|---|---|---|---|---|---|
| Strains | -Lactamase content | IPM[a] | ETP | MEM | SUPERCARBA | ChromID ESBL | CHROMagar KPC |
| Non-carbapenemase producers | | | | | | | |
| K. pneumoniae 7725 | SHV-1 | 0.19 | 0.006 | 0.032 | $\geq 1 \times 10^8$ | $\geq 1 \times 10^8$ | $\geq 1 \times 10^8$ |
| K. pneumoniae 0227 | SHV-1 | 0.19 | 0.008 | 0.016 | $\geq 1 \times 10^8$ | $\geq 1 \times 10^8$ | $\geq 1 \times 10^8$ |
| K. pneumoniae 648236[d] | SHV-2a | 0.25 | 2 | 0.38 | $1 \times 10^2$ | $1 \times 10^1$ | $\geq 1 \times 10^8$ |
| K. pneumoniae 1022 | SHV-2a + SHV-28 | 0.5 | 0.016 | 0.023 | $\geq 1 \times 10^8$ | $1 \times 10^1$ | $\geq 1 \times 10^8$ |
| K. pneumoniae BER[d] | SHV-28 + TEM-1 | 1 | 4 | 1 | $1 \times 10^2$ | $1 \times 10^3$ | $1 \times 10^3$ |
| K. pneumoniae KPN | CTX-M-15 | 0.12 | 0.012 | 0.012 | $1 \times 10^7$ | $1 \times 10^1$ | $\geq 1 \times 10^8$ |
| K. pneumoniae 10112 | CTX-M-15 + TEM-1 + SHV-11 | 0.5 | 0.016 | 0.023 | $6 \times 10^7$ | $1 \times 10^1$ | $\geq 1 \times 10^8$ |
| K. pneumoniae 1025 | CTX-M-14 + TEM-1 + SHV-11 | 0.12 | 0.016 | 0.016 | $\geq 1 \times 10^8$ | $1 \times 10^1$ | $\geq 1 \times 10^8$ |
| K. pneumoniae MEK[d] | CTX-M-15 + SHV-11 | 1.5 | >32 | 6 | $1 \times 10^1$ | $1 \times 10^1$ | $1 \times 10^1$ |
| K. pneumoniae SIM[d] | CTX-M-15 + TEM-1 + SHV-1 | 8 | >32 | 6 | $1 \times 10^1$ | $1 \times 10^1$ | $1 \times 10^2$ |
| K. pneumoniae SHM[d] | CTX-M-15 + TEM-1 + SHV-11 | 3 | >32 | 3 | $1 \times 10^1$ | $1 \times 10^1$ | $1 \times 10^1$ |
| K. pneumoniae COO[d] | CTX-M-15 + SHV-28 | 8 | >32 | 4 | $1 \times 10^1$ | $1 \times 10^1$ | $1 \times 10^1$ |
| K. pneumoniae FOS[d] | CTX-M-15 + TEM-1 + SHV-11 | 6 | >32 | >32 | $1 \times 10^2$ | $1 \times 10^1$ | $1 \times 10^1$ |
| K. pneumoniae BED[d] | CTX-M-15 + TEM-1 + SHV-11 | 1.5 | >32 | 4 | $1 \times 10^1$ | $1 \times 10^1$ | $1 \times 10^1$ |
| K. pneumoniae SHI[d] | CTX-M-15 + TEM-1 + SHV-11 | 0.25 | 1 | 1 | $7 \times 10^4$ | $1 \times 10^1$ | $\geq 1 \times 10^8$ |
| K. pneumoniae LEG[d] | CTX-M-15 + TEM-1 + SHV-12 | 0.75 | >32 | 3 | $2 \times 10^4$ | $2 \times 10^1$ | $2 \times 10^1$ |
| K. pneumoniae ALE[d] | CTX-M-15 + SHV-1 | 1 | >32 | 4 | $1 \times 10^5$ | $1 \times 10^1$ | $1 \times 10^1$ |
| K. pneumoniae KDH[e] | DHA-2 | 0.12 | 0.5 | 0.12 | $1 \times 10^2$ | $1 \times 10^1$ | $\geq 1 \times 10^8$ |
| E. coli 6252 | (wild type) | 0.12 | 0.004 | 0.008 | $\geq 1 \times 10^8$ | $\geq 1 \times 10^8$ | $\geq 1 \times 10^8$ |
| E. coli 6367 | (wild type) | 0.19 | 0.006 | 0.012 | $\geq 1 \times 10^8$ | $\geq 1 \times 10^8$ | $\geq 1 \times 10^8$ |
| E. coli 1082 | TEM-1 | 0.19 | 0.019 | 0.016 | $\geq 1 \times 10^8$ | $\geq 1 \times 10^8$ | $\geq 1 \times 10^8$ |
| E. coli 1034 | TEM-1 + SHV-38 | 0.19 | 0.006 | 0.016 | $\geq 1 \times 10^8$ | $\geq 1 \times 10^8$ | $\geq 1 \times 10^8$ |
| E. coli 1048 | TEM-1 + SHV-2a | 0.19 | 0.012 | 0.016 | $\geq 1 \times 10^8$ | $1 \times 10^1$ | $\geq 1 \times 10^8$ |
| E. coli 1008 | CTX-M-1 + TEM-1 | 0.19 | 0.016 | 0.016 | $\geq 1 \times 10^8$ | $1 \times 10^1$ | $\geq 1 \times 10^8$ |
| E. coli 10122 | CTX-M-1 + TEM-1 | 0.19 | 0.016 | 0.016 | $\geq 1 \times 10^8$ | $1 \times 10^1$ | $\geq 1 \times 10^8$ |
| E. coli 1020 | CTX-M-1 + TEM-1 | 0.19 | 0.023 | 0.016 | $\geq 1 \times 10^8$ | $1 \times 10^1$ | $\geq 1 \times 10^8$ |
| E. coli 10121 | CTX-M-2 | 0.19 | 0.016 | 0.016 | $\geq 1 \times 10^8$ | $1 \times 10^1$ | $\geq 1 \times 10^8$ |
| E. coli 1023 | CTX-M-2 + TEM-1 | 0.12 | 0.016 | 0.016 | $\geq 1 \times 10^8$ | $1 \times 10^1$ | $\geq 1 \times 10^8$ |
| E. coli E14 | CTX-M-14 | 0.12 | 0.012 | 0.012 | $\geq 1 \times 10^8$ | $1 \times 10^1$ | $\geq 1 \times 10^8$ |
| E. coli FOR | CTX-M-15 | 0.12 | 0.012 | 0.012 | $\geq 1 \times 10^8$ | $1 \times 10^1$ | $\geq 1 \times 10^8$ |
| E. coli 1033 | CTX-M-15 | 0.19 | 0.012 | 0.016 | $\geq 1 \times 10^8$ | $1 \times 10^1$ | $\geq 1 \times 10^8$ |
| E. coli EVB | VEB-1 | 0.12 | 0.012 | 0.012 | $\geq 1 \times 10^8$ | $1 \times 10^1$ | $\geq 1 \times 10^8$ |
| E. coli 1092 | OXA-1 | 0.12 | 0.19 | 0.023 | $\geq 1 \times 10^8$ | $1 \times 10^1$ | $\geq 1 \times 10^8$ |
| E. coli ECA | ACC-1 | 0.12 | 0.012 | 0.012 | $\geq 1 \times 10^8$ | $5 \times 10^3$ | $\geq 1 \times 10^8$ |
| E. coli SYD | CMY-2 | 0.12 | 0.012 | 0.012 | $\geq 1 \times 10^8$ | $1 \times 10^1$ | $\geq 1 \times 10^8$ |
| E. coli MET | Chromosome-encoded extended-spectrum cephalosporinase | 0.12 | 0.012 | 0.012 | $\geq 1 \times 10^8$ | $1 \times 10^1$ | $\geq 1 \times 10^8$ |
| E. coli MAR[e] | Overexpressed AmpC | 16 | >32 | 2 | $1 \times 10^2$ | $1 \times 10^1$ | $1 \times 10^1$ |
| E. coli HB4[d] | (OmpC-, OmpF-) | 0.12 | 1 | 0.25 | $1 \times 10^1$ | $\geq 1 \times 10^8$ | $\geq 1 \times 10^8$ |
| E. aerogenes 1009 | TEM-24 | 0.19 | 0.12 | 0.016 | $\geq 1 \times 10^8$ | $1 \times 10^1$ | $\geq 1 \times 10^8$ |
| E. aerogenes 1085 | TEM-24 | 0.12 | 0.19 | 0.023 | $\geq 1 \times 10^8$ | $1 \times 10^1$ | $\geq 1 \times 10^8$ |
| E. cloacae 7746 | (wild type) | 0.38 | 0.064 | 0.032 | $\geq 1 \times 10^8$ | $\geq 1 \times 10^8$ | $\geq 1 \times 10^8$ |
| E. cloacae 7725 | (wild type) | 0.19 | 0.008 | 0.012 | $\geq 1 \times 10^8$ | $\geq 1 \times 10^8$ | $\geq 1 \times 10^8$ |
| E. cloacae 5434 | (wild type) | 0.38 | 0.016 | 0.032 | $\geq 1 \times 10^8$ | $\geq 1 \times 10^8$ | $\geq 1 \times 10^8$ |
| E. cloacae 1012 | TEM-1 + SHV-12 | 0.19 | 0.016 | 0.016 | $\geq 1 \times 10^8$ | $1 \times 10^1$ | $\geq 1 \times 10^8$ |
| E. cloacae 1072[e] | TEM-1 + OXA-1 | 0.38 | 0.5 | 0.064 | $\geq 1 \times 10^8$ | $1 \times 10^1$ | $\geq 1 \times 10^8$ |
| E. cloacae CLO | CTX-M-15 | 0.12 | 0.12 | 0.12 | $1 \times 10^7$ | $1 \times 10^1$ | $\geq 1 \times 10^8$ |
| E. cloacae 10111[e] | TEM-1 + CTX-M-15 | 0.5 | 0.75 | 0.094 | $\geq 1 \times 10^8$ | $1 \times 10^1$ | $\geq 1 \times 10^8$ |
| E. cloacae 1027 | TEM-1 + CTX-M-15 | 0.19 | 0.016 | 0.016 | $\geq 1 \times 10^8$ | $1 \times 10^1$ | $\geq 1 \times 10^8$ |
| E. cloacae CVB | VEB-1 | 0.12 | 0.12 | 0.12 | $1 \times 10^4$ | $1 \times 10^1$ | $\geq 1 \times 10^8$ |
| E. cloacae 1019[e] | TEM-1 | 0.25 | 1 | 0.094 | $\geq 1 \times 10^8$ | $1 \times 10^1$ | $\geq 1 \times 10^8$ |
| E. cloacae ARF[e] | Overexpressed AmpC | 0.12 | 1 | 0.12 | $1 \times 10^7$ | $1 \times 10^1$ | $\geq 1 \times 10^8$ |
| E. cloacae BLA[e] | Overexpressed AmpC | 0.12 | 1 | 0.12 | $1 \times 10^7$ | $1 \times 10^1$ | $\geq 1 \times 10^8$ |
| E. cloacae CON[e] | Overexpressed AmpC | 0.25 | 4 | 0.25 | $1 \times 10^7$ | $1 \times 10^1$ | $\geq 1 \times 10^8$ |
| E. cloacae AZA[e] | Overexpressed AmpC | 0.12 | 1 | 0.12 | $1 \times 10^7$ | $1 \times 10^6$ | $\geq 1 \times 10^8$ |
| C. freundii 7767 | (wild type) | 0.25 | 0.008 | 0.016 | $\geq 1 \times 10^8$ | $\geq 1 \times 10^8$ | $\geq 1 \times 10^8$ |
| C. freundii 10107 | TEM-1 + SHV-12 | 0.38 | 0.016 | 0.023 | $\geq 1 \times 10^8$ | $1 \times 10^1$ | $\geq 1 \times 10^8$ |
| C. freundii 1003 | CTX-M-15 + TEM-1 | 0.38 | 0.016 | 0.023 | $\geq 1 \times 10^8$ | $1 \times 10^1$ | $\geq 1 \times 10^8$ |
| C. freundii 10135 | CTX-M-15 | 0.38 | 0.016 | 0.023 | $\geq 1 \times 10^8$ | $1 \times 10^1$ | $\geq 1 \times 10^8$ |
| C. freundii MAU[e] | Overexpressed AmpC + TEM-3 | 1 | 8 | 1 | $1 \times 10^5$ | $1 \times 10^1$ | $1 \times 10^5$ |
| S. typhimurium 1081 | CTX-M-1 | 0.25 | 0.19 | 0.032 | $\geq 1 \times 10^8$ | $1 \times 10^1$ | $\geq 1 \times 10^8$ |

TABLE 2-continued

Limit of detection of SUPERCARBA medium for 176 carbapenemase- and/or ESBL/AmpC-producing enterobacterial isolates as compared to those obtained with ChromID ESBL and CHROMagar KPC media. MIC values of imipenem, ertapenem and meropenem are provided for each strain.

| Strains | -Lactamase content | MIC (µg/ml) | | | Lowest detection limit (CFU/ml) | | |
| --- | --- | --- | --- | --- | --- | --- | --- |
| | | IPM[a] | ETP | MEM | SUPERCARBA | ChromID ESBL | CHROMagar KPC |
| P. mirabilis 1031 | CTX-M-14 + TEM-1 + SHV-11 | 1.5 | 0.047 | 0.032 | $\geq 1 \times 10^8$ | $1 \times 10^1$ | $\geq 1 \times 10^8$ |
| P. mirabilis PMA | ACC-1 | 0.25 | 0.094 | 0.064 | $\geq 1 \times 10^8$ | $\geq 1 \times 10^8$ | $\geq 1 \times 10^8$ |

[a]Abbreviations: IMP, imipenem; ETP, ertapenem; MP, meropenem.
[b]Boldened β-lactamase name correspond to carbapenemase.
[c]Underligned CFU counts are considered as negative results (cut off values set at $\geq 1 \times 10^3$ CFU/ml)
[d]Reduced susceptibility to ertapenem due to porin deficiency.
[e]Reduced susceptibility to ertapenem due to overexpressed AmpC.

TABLE 3

Sensitivity and specificity of SUPERCARBA, ChromID ESBL, and CHROMagar KPC media[a]

| | SUPERCARBA | ChromID ESBL | CHROMagar KPC |
| --- | --- | --- | --- |
| SN (%)[a] | 95.6 | 87.7 | 40.3 |
| SP (%) | 82.2 | 24.2 | 85.5 |
| SN class A[b] | 100 | 100 | 66.7 |
| SN class B | 90 | 98 | 55.8 |
| SN class D | 100 | 70 | 13.6 |

[a]Abbreviations: SN, sensitivity; SP, specificity.
[b]Sensitivity was determined for each Ambler class of carbapenemase: class A are of KPC-type, class B of VIM, IMP, and NDM-type, whereas class D are of OXA-48-type.

TABLE 4

Limit of detection of SUPERCARBA medium for 21 carbapenemase- and/or ESBL/AmpC-producing enterobacterial isolates as compared to those obtained with modified-SUPERCARBA, i.e. with Trypticase-soy agar supplemented with vancomycin (20 µg/ml) and amphotericin B (30 µg/ml) replacing Drigalski agar. MIC values of imipenem, ertapenem and meropenem are provided for each strain.

| Strains | -Lactamase content | MIC (µg/ml) | | | Lowest detection limit (CFU/ml) | |
| --- | --- | --- | --- | --- | --- | --- |
| | | IPM[a] | ETP | MEM | ETP Cloxa -Zinc SUPERCARBA | TSA-Vanco-Ampho-modified SUPERCARBA |
| Ambler class A carbapenemases | | | | | | |
| K. pneumoniae MUS | KPC-2 + TEM-1 + SHV-11 + SHV-12 | 0.75 | 4 | 1.5 | $1 \times 10^1$ | $1 \times 10^1$ |
| E. cloacae HPTU | KPC-2 + TEM-1 + SHV-11 | 2 | 4 | 1.5 | $1 \times 10^1$ | $1 \times 10^1$ |
| Ambler class B carbapenemases | | | | | | |
| K. pneumoniae OMA419 | NDM-1 + OXA-1 | 1.5 | 6 | 2 | $1 \times 10^1$ | $1 \times 10^1$ |
| K. pneumoniae OM2 | NDM-1 + TEM-1 + CTX-M-3 + SHV-11 + OXA-1 | 0.75 | 8 | 1.5 | $1 \times 10^1$ | $1 \times 10^1$ |
| P. stuartii PS1 | NDM-1 + CMY-6 + OXA-1 | 12 | 0.38 | 1.5 | $1 \times 10^7$ | $1 \times 10^3$ |
| E. coli JAP | IMP-1 | 0.5 | 3 | 0.5 | $1 \times 10^4$ | $2 \times 10^1$ |
| E. cloacae TAW | IMP-8 + SHV-12 | 0.75 | 0.5 | 0.5 | $1 \times 10^2$ | $2 \times 10^2$ |
| Ambler class D carbapenemases | | | | | | |
| K. pneumoniae SCO | OXA-48 | 0.5 | 0.75 | 0.25 | $1 \times 10^1$ | $1 \times 10^1$ |
| K. pneumoniae BEN | OXA-48 + TEM-1 + CTX-M-15 + SHV-28 | 0.38 | 1 | 0.25 | $1 \times 10^1$ | $1 \times 10^1$ |
| E. coli ROB | OXA-48 | 0.5 | 0.75 | 0.25 | $2 \times 10^1$ | $1 \times 10^1$ |
| E. coli AME | OXA-48 + CTX-M-24 | 0.25 | 0.5 | 0.19 | $2 \times 10^1$ | $1 \times 10^1$ |
| E. cloacae TUR | OXA-48 + SHV-5 | 0.5 | 0.5 | 0.5 | $1 \times 10^1$ | $1 \times 10^1$ |
| C. koseri VER | OXA-48 | 0.75 | 2 | 0.38 | $1 \times 10^1$ | $1 \times 10^1$ |
| K. pneumoniae HOL | OXA-181 + CTX-M-15 | 1 | 4 | 1 | $1 \times 10^1$ | $1 \times 10^2$ |
| P. rettgeri RAP | OXA-181 + OXA-1 | 8 | 1 | 2 | $5 \times 10^2$ | $1 \times 10^1$ |

TABLE 4-continued

Limit of detection of SUPERCARBA medium for 21 carbapenemase- and/or ESBL/AmpC-producing enterobacterial isolates as compared to those obtained with modified-SUPERCARBA, i.e. with Trypticase-soy agar supplemented with vancomycin (20 µg/ml) and amphotericin B (30 µg/ml) replacing Drigalski agar. MIC values of imipenem, ertapenem and meropenem are provided for each strain.

| | | MIC (µg/ml) | | | Lowest detection limit (CFU/ml) | |
|---|---|---|---|---|---|---|
| | | | | | ETP Cloxa -Zinc | TSA-Vanco-Ampho-modified |
| Strains | -Lactamase content | IPM$^a$ | ETP | MEM | SUPERCARBA | SUPERCARBA |
| Non-carbapenemase producers | | | | | | |
| K. pneumoniae 7725 | SHV-1 | 0.19 | 0.006 | 0.032 | $>1 \times 10^8$ | $>1 \times 10^8$ |
| K. pneumoniae 648236$^d$ | SHV-2a | 0.25 | 2 | 0.38 | $1 \times 10^2$ | $3 \times 10^1$ |
| E. coli 1034 | TEM-1 + SHV-38 | 0.19 | 0.006 | 0.016 | $>1 \times 10^8$ | $>1 \times 10^8$ |
| E. coli 1008 | TEM-1 + CTX-M-1 | 0.19 | 0.016 | 0.016 | $>1 \times 10^8$ | $>1 \times 10^8$ |
| E. coli HB4$^d$ | (OmpC-, OmpF-) | 0.12 | 1 | 0.25 | $1 \times 10^1$ | $1 \times 10^1$ |
| C. freundii MAU$^e$ | Overexpressed AmpC + TEM-3 | 1 | 8 | 1 | $1 \times 10^5$ | $1 \times 10^1$ |

TABLE 5

Sensitivity and specificity of SUPERCARBA and SUPERCARBA-modified with TSA-Vanco-Ampho replacing Drigalski agar

| | Detection medium | |
|---|---|---|
| | Drig- ETP Cloxa -Zinc SUPERCARBA | TSA-Vanco- Ampho- modified SUPERCARBA |
| SN (%)$^a$ | 86.7 | 93.3 |
| SP (%) | 66.7 | 50 |

$^a$Abbreviations: SN, sensitivity; SP, specificity.

TABLE 6

Limit of detection of SUPERCARBA medium for 40 carbapenemase- and/or ESBL/AmpC-producing enterobacterial isolates as compared to those obtained with modified-SUPERCARBA, i.e. with doripenem 0.012, 0.024 or 0.048 µg/ml replacing ertapenem. MIC values of imipenem, ertapenem and meropenem are provided for each strain.

| | | MIC (µg/ml) | | | Lowest detection limit (CFU/ml) | | | |
|---|---|---|---|---|---|---|---|---|
| | | | | | ETP Cloxa Zinc | DORI 0.048 Cloxa | DORI 0.024 Cloxa | DORI 0.012 Cloxa |
| Strains | β-Lactamase content | IPM$^a$ | ETP | MEM | (SUPERCARBA) | Zinc | Zinc | Zinc |
| Ambler class B carbapenemases | | | | | | | | |
| E. coli JAP | IMP-1 | 0.5 | 3 | 0.5 | $1 \times 10^4$ | $8 \times 10^4$ | $8 \times 10^4$ | $4 \times 10^2$ |
| E. cloacae TAW | IMP-8 + SHV-12 | 0.75 | 0.5 | 0.5 | $1 \times 10^2$ | $1 \times 10^2$ | $3 \times 10^1$ | $1 \times 10^1$ |
| Ambler class D carbapenemases | | | | | | | | |
| K. pneumoniae BEL | OXA-48 | 1 | 4 | 1 | $1 \times 10^1$ | $2 \times 10^1$ | $1 \times 10^1$ | $1 \times 10^1$ |
| K. pneumoniae SCO | OXA-48 | 0.5 | 0.75 | 0.25 | $1 \times 10^1$ | $1 \times 10^1$ | $1 \times 10^1$ | $1 \times 10^1$ |
| K. pneumoniae ROU | OXA-48 + CTX-M-15 | 0.5 | 1.5 | 0.25 | $1 \times 10^1$ | $1 \times 10^4$ | $1 \times 10^1$ | $4 \times 10^4$ |
| K. pneumoniae BAJ | OXA-48 + TEM-1 + CTX-M-15 + SHV-28 | 0.5 | 1.5 | 0.38 | $1 \times 10^1$ | $1 \times 10^1$ | $1 \times 10^1$ | $2 \times 10^1$ |
| K. pneumoniae BEN | OXA-48 + TEM-1 + CTX-M-15 + SHV-28 | 0.38 | 1 | 0.25 | $1 \times 10^1$ | $2 \times 10^1$ | $1 \times 10^1$ | $1 \times 10^1$ |
| K. pneumoniae SIC | OXA-48 + CTX-M-15 + SHV-28 | 0.25 | 1 | 0.25 | $1 \times 10^1$ | $2 \times 10^2$ | $1 \times 10^2$ | $1 \times 10^1$ |
| K. pneumoniae AMS | OXA-48 + TEM-1 + CTX-M-15 + OXA-1 | 0.5 | 2 | 0.38 | $1 \times 10^1$ | $2 \times 10^1$ | $1 \times 10^1$ | $2 \times 10^1$ |
| K. pneumoniae ELK | OXA-48 + TEM-1 + CTX-M-15 + SHV-11 | 0.5 | 3 | 0.38 | $1 \times 10^1$ | $2 \times 10^2$ | $1 \times 10^1$ | $2 \times 10^1$ |
| K. pneumoniae VSG | OXA-48 + TEM-1 + CTX-M-15 + OXA-1 | 0.75 | 3 | 0.75 | $1 \times 10^1$ | $2 \times 10^1$ | $2 \times 10^1$ | $1 \times 10^1$ |
| E. coli ROB | OXA-48 | 0.5 | 0.75 | 0.25 | $2 \times 10^1$ | $2 \times 10^1$ | $1 \times 10^1$ | $1 \times 10^1$ |
| E. coli BOU | OXA-48 + CTX-M-15 | 0.5 | 0.75 | 0.125 | $2 \times 10^1$ | $1 \times 10^4$ | $1 \times 10^1$ | $1 \times 10^1$ |

TABLE 6-continued

Limit of detection of SUPERCARBA medium for 40 carbapenemase- and/or ESBL/AmpC-producing enterobacterial isolates as compared to those obtained with modified-SUPERCARBA, i.e. with doripenem 0.012, 0.024 or 0.048 µg/ml replacing ertapenem. MIC values of imipenem, ertapenem and meropenem are provided for each strain.

| | | | | | Lowest detection limit (CFU/ml) | | | |
|---|---|---|---|---|---|---|---|---|
| | | | | | ETP Cloxa Zinc (SUPERCARBA) | DORI 0.048 Cloxa Zinc | DORI 0.024 Cloxa Zinc | DORI 0.012 Cloxa Zinc |
| Strains | β-Lactamase content | IPM$^a$ | ETP | MEM | | | | |
| MIC (µg/ml) | | | | | | | | |
| E. coli AME | OXA-48 + CTX-M-24 | 0.25 | 0.5 | 0.19 | $2 \times 10^1$ | $2 \times 10^6$ | $2 \times 10^1$ | $1 \times 10^1$ |
| E. coli BON | OXA-48 + TEM-1 + CTX-M-24 | 0.38 | 0.5 | 0.19 | $1 \times 10^1$ | $2 \times 10^5$ | $2 \times 10^1$ | $1 \times 10^1$ |
| E. cloacae TUR | OXA-48 + SHV-5 | 0.5 | 0.5 | 0.5 | $1 \times 10^1$ | $1 \times 10^1$ | $1 \times 10^1$ | $1 \times 10^1$ |
| C. koseri VER | OXA-48 | 0.75 | 2 | 0.38 | $1 \times 10^1$ | $3 \times 10^2$ | $3 \times 10^1$ | $1 \times 10^1$ |
| K. pneumoniae HOL | OXA-181 + CTX-M-15 | 1 | 4 | 1 | $1 \times 10^1$ | $1 \times 10^1$ | $1 \times 10^1$ | $1 \times 10^2$ |
| K. pneumoniae OMA | OXA-181 + CTXM-15 + OXA-1 | 0.5 | 2 | 0.5 | $1 \times 10^1$ | $1 \times 10^1$ | $1 \times 10^1$ | $4 \times 10^1$ |
| Non-carbapenemase producers | | | | | | | | |
| K. pneumoniae 7725 | SHV-1 | 0.19 | 0.006 | 0.032 | $\geq 1 \times 10^8$ | $\geq 1 \times 10^8$ | $\geq 1 \times 10^8$ | $2 \times 10^2$ |
| K. pneumoniae 648236$^d$ | SHV-2a | 0.25 | 2 | 0.38 | $1 \times 10^2$ | $1 \times 10^1$ | $1 \times 10^1$ | $2 \times 10^1$ |
| K. pneumoniae BER$^d$ | SHV-28 + TEM-1 | 1 | 4 | 1 | $1 \times 10^2$ | $1 \times 10^2$ | $1 \times 10^2$ | $1 \times 10^1$ |
| K. pneumoniae 1025 | CTX-M-14 + TEM-1 + SHV-11 | 0.12 | 0.016 | 0.016 | $\geq 1 \times 10^8$ | $\geq 1 \times 10^8$ | $\geq 1 \times 10^8$ | $1 \times 10^1$ |
| K. pneumoniae KDH$^e$ | DHA-2 | 0.12 | 0.5 | 0.12 | $1 \times 10^2$ | $1 \times 10^1$ | $1 \times 10^1$ | $1 \times 10^1$ |
| E. coli 1034 | TEM-1 + SHV-38 | 0.19 | 0.006 | 0.016 | $\geq 1 \times 10^8$ | $\geq 1 \times 10^8$ | $\geq 1 \times 10^8$ | $1 \times 10^1$ |
| E. coli 1048 | TEM-1 + SHV-2a | 0.19 | 0.012 | 0.016 | $\geq 1 \times 10^8$ | $\geq 1 \times 10^8$ | $\geq 1 \times 10^8$ | $1 \times 10^5$ |
| E. coli 10121 | CTX-M-2 | 0.19 | 0.016 | 0.016 | $\geq 1 \times 10^8$ | $\geq 1 \times 10^8$ | $\geq 1 \times 10^8$ | $3 \times 10^5$ |
| E. coli SYD | CMY-2 | 0.12 | 0.012 | 0.012 | $\geq 1 \times 10^8$ | $\geq 1 \times 10^8$ | $\geq 1 \times 10^8$ | $3 \times 10^3$ |
| E. coli MAR$^e$ | Overexpressed AmpC | 16 | >32 | 2 | $1 \times 10^2$ | $\geq 1 \times 10^8$ | $\geq 1 \times 10^8$ | $6 \times 10^2$ |
| E. coli HB4$^d$ | (OmpC-, OmpF-) | 0.12 | 1 | 0.25 | $1 \times 10^1$ | $\geq 1 \times 10^8$ | $1 \times 10^4$ | $6 \times 10^2$ |
| E. aerogenes 1085 | TEM-24 | 0.12 | 0.19 | 0.023 | $\geq 1 \times 10^8$ | $\geq 1 \times 10^8$ | $\geq 1 \times 10^8$ | $2 \times 10^1$ |
| E. cloacae 5434 | (wild type) | 0.38 | 0.016 | 0.032 | $\geq 1 \times 10^8$ | $1 \times 10^6$ | $1 \times 10^2$ | $1 \times 10^1$ |
| E. cloacae CVB | VEB-1 | 0.12 | 0.12 | 0.12 | $1 \times 10^4$ | $\geq 1 \times 10^8$ | $1 \times 10^5$ | $6 \times 10^1$ |
| E. cloacae CON$^e$ | Overexpressed AmpC | 0.12 | 1 | 0.12 | $1 \times 10^7$ | $\geq 1 \times 10^8$ | $\geq 1 \times 10^8$ | $6 \times 10^1$ |
| E. cloacae BLA$^e$ | Overexpressed AmpC | 0.12 | 1 | 0.12 | $1 \times 10^7$ | $\geq 1 \times 10^8$ | $1 \times 10^7$ | $1 \times 10^2$ |
| C. freundii 7767 | (wild type) | 0.25 | 0.008 | 0.016 | $\geq 1 \times 10^8$ | $\geq 1 \times 10^8$ | $\geq 1 \times 10^8$ | $1 \times 10^2$ |
| C. freundii 10107 | TEM-1 + SHV-12 | 0.38 | 0.016 | 0.023 | $\geq 1 \times 10^8$ | $\geq 1 \times 10^8$ | $\geq 1 \times 10^8$ | $2 \times 10^2$ |
| C. freundii 10135 | CTX-M-15 | 0.38 | 0.016 | 0.023 | $\geq 1 \times 10^8$ | $\geq 1 \times 10^8$ | $\geq 1 \times 10^8$ | $3 \times 10^1$ |
| C. freundii MAU$^e$ | Overexpressed AmpC + TEM-3 | 1 | 8 | 1 | $1 \times 10^5$ | $5 \times 10^2$ | $3 \times 10^1$ | $1 \times 10^2$ |
| S. typhimurium 1081 | CTX-M-1 | 0.25 | 0.19 | 0.032 | $\geq 1 \times 10^8$ | $\geq 1 \times 10^8$ | $\geq 1 \times 10^8$ | $4 \times 10^1$ |

TABLE 7

Sensitivity and specificity of SUPERCARBA, and modified SUPERCARBA with doripenem 0.012, 0.024, or 0.048 µg/ml replacing ertapenem 0.25 µg/ml.$^a$

| Detection medium | | | |
|---|---|---|---|
| ETP Cloxa Zinc (SUPERCARBA) | DORI 0.048 Cloxa Zinc | DORI 0.024 Cloxa Zinc | DORI 0.012 Cloxa Zinc |
| SN (%)$^a$ 94.7 | 73.7 | 94.7 | 94.7 |
| SN class D 100 | 76.5 | 100 | 94.1 |
| SP (%) 76.2 | 80.9 | 76.2 | 14.3 |

$^a$Abbreviations: SN, sensitivity; SP, specificity.
$^b$Sensitivity was determined for each Ambler class of carbapenemase.

TABLE 8

Limit of detection of SUPERCARBA medium for 60 carbapenemase- and/or ESBL/AmpC-producing enterobacterial isolates as compared to those obtained with modified-SUPERCARBA, i.e. with oxacillin replacing cloxacillin. MIC values of imipenem, ertapenem and meropenem are provided for each strain.

| | | MIC (μg/ml) | | | Lowest detection limit (CFU/ml) | |
|---|---|---|---|---|---|---|
| Strains | -Lactamase content | IPM[a] | ETP | MEM | ETP Cloxa Zinc (SUPERCARBA) | ETP Oxa Zinc |
| Ambler class A carbapenemases (KPC) | | | | | | |
| K. pneumoniae MUS | KPC-2 + TEM-1 + SHV-11 + SHV-12 | 0.75 | 4 | 1.5 | $1 \times 10^1$ | $2 \times 10^1$ |
| E. cloacae HPTU | KPC-2 + TEM-1 + SHV-11 | 2 | 4 | 1.5 | $1 \times 10^1$ | $1 \times 10^1$ |
| Ambler class B carbapenemases | | | | | | |
| K. pneumoniae OMA419 | NDM-1 + OXA-1 | 1.5 | 6 | 2 | $1 \times 10^1$ | $1 \times 10^1$ |
| K. pneumoniae OM2 | NDM-1 + TEM-1 + CTX-M-3 + SHV-11 + OXA-1 | 0.75 | 8 | 1.5 | $1 \times 10^1$ | $1 \times 10^1$ |
| P. stuartii PS1 | NDM-1 + CMY-6 + OXA-1 | 12 | 0.38 | 1.5 | $1 \times 10^7$ | $\geq 5 \times 10^7$ |
| E. coli JAP | IMP-1 | 0.5 | 3 | 0.5 | $1 \times 10^4$ | $4 \times 10^4$ |
| E. cloacae TAW | IMP-8 + SHV-12 | 0.75 | 0.5 | 0.5 | $1 \times 10^2$ | $2 \times 10^1$ |
| Ambler class D carbapenemases | | | | | | |
| K. pneumoniae BEL | OXA-48 | 1 | 4 | 1 | $1 \times 10^1$ | $1 \times 10^1$ |
| K. pneumoniae SCO | OXA-48 | 0.5 | 0.75 | 0.25 | $1 \times 10^1$ | $1 \times 10^1$ |
| K. pneumoniae ROU | OXA-48 + CTX-M-15 | 0.5 | 1.5 | 0.25 | $1 \times 10^1$ | $2 \times 10^1$ |
| K. pneumoniae BAJ | OXA-48 + TEM-1 + CTX-M-15 + SHV-28 | 0.5 | 1.5 | 0.38 | $1 \times 10^1$ | $1 \times 10^1$ |
| K. pneumoniae BEN | OXA-48 + TEM-1 + CTX-M-15 + SHV-28 | 0.38 | 1 | 0.25 | $1 \times 10^1$ | $1 \times 10^1$ |
| K. pneumoniae SIC | OXA-48 + CTX-M-15 + SHV-28 | 0.25 | 1 | 0.25 | $1 \times 10^1$ | $1 \times 10^1$ |
| K. pneumoniae AMS | OXA-48 + TEM-1 + CTX-M-15 + OXA-1 | 0.5 | 2 | 0.38 | $1 \times 10^1$ | $2 \times 10^1$ |
| K. pneumoniae ELK | OXA-48 + TEM-1 + CTX-M-15 + SHV-11 | 0.5 | 3 | 0.38 | $1 \times 10^1$ | $1 \times 10^1$ |
| K. pneumoniae VSG | OXA-48 + TEM-1 + CTX-M-15 + OXA-1 | 0.75 | 3 | 0.75 | $1 \times 10^1$ | $1 \times 10^1$ |
| E. coli ROB | OXA-48 | 0.5 | 0.75 | 0.25 | $2 \times 10^1$ | $6 \times 10^1$ |
| E. coli BOU | OXA-48 + CTX-M-15 | 0.5 | 0.75 | 0.125 | $2 \times 10^1$ | $1 \times 10^1$ |
| E. coli AME | OXA-48 + CTX-M-24 | 0.25 | 0.5 | 0.19 | $2 \times 10^1$ | $1 \times 10^1$ |
| E. coli BON | OXA-48 + TEM-1 + CTX-M-24 | 0.38 | 0.5 | 0.19 | $1 \times 10^1$ | $2 \times 10^1$ |
| E. cloacae TUR | OXA-48 + SHV-5 | 0.5 | 0.5 | 0.5 | $1 \times 10^1$ | $1 \times 10^1$ |
| C. koseri VER | OXA-48 | 0.75 | 2 | 0.38 | $1 \times 10^1$ | $2 \times 10^1$ |
| K. pneumoniae HOL | OXA-181 + CTX-M-15 | 1 | 4 | 1 | $1 \times 10^1$ | $1 \times 10^2$ |
| K. pneumoniae OMA | OXA-181 + CTXM-15 + OXA-1 | 0.5 | 2 | 0.5 | $1 \times 10^1$ | $3 \times 10^1$ |
| P. rettgeri RAP | OXA-181 + OXA-1 | 8 | 1 | 2 | $5 \times 10^2$ | $5 \times 10^1$ |
| Non-carbapenemase producers | | | | | | |
| K. pneumoniae 7725 | SHV-1 | 0.19 | 0.006 | 0.032 | $\geq 1 \times 10^8$ | $\geq 1 \times 10^8$ |
| K. pneumoniae 648236[d] | SHV-2a | 0.25 | 2 | 0.38 | $1 \times 10^2$ | $3 \times 10^1$ |
| K. pneumoniae BER[d] | SHV-28 + TEM-1 | 1 | 4 | 1 | $1 \times 10^2$ | $1 \times 10^2$ |
| K. pneumoniae 1025 | CTX-M-14 + TEM-1 + SHV-11 | 0.12 | 0.016 | 0.016 | $\geq 1 \times 10^8$ | $\geq 1 \times 10^8$ |
| K. pneumoniae BED[d] | CTX-M-15 + TEM-1 + SHV-11 | 1.5 | >32 | 4 | $1 \times 10^1$ | $4 \times 10^1$ |
| K. pneumoniae ALE[d] | CTX-M-15 + SHV-1 | 1 | >32 | 4 | $1 \times 10^5$ | $1 \times 10^5$ |
| K. pneumoniae KDH[e] | DHA-2 | 0.12 | 0.5 | 0.12 | $1 \times 10^2$ | $1 \times 10^1$ |
| E. coli 6367 | (wild type) | 0.19 | 0.006 | 0.012 | $\geq 1 \times 10^8$ | $\geq 1 \times 10^8$ |
| E. coli 1082 | TEM-1 | 0.19 | 0.019 | 0.016 | $\geq 1 \times 10^8$ | $\geq 1 \times 10^8$ |
| E. coli 1034 | TEM-1 + SHV-38 | 0.19 | 0.006 | 0.016 | $\geq 1 \times 10^8$ | $\geq 1 \times 10^8$ |
| E. coli 1048 | TEM-1 + SHV-2a | 0.19 | 0.012 | 0.016 | $\geq 1 \times 10^8$ | $\geq 1 \times 10^8$ |
| E. coli 1008 | TEM-1 + CTX-M-1 | 0.19 | 0.016 | 0.016 | $\geq 1 \times 10^8$ | $\geq 1 \times 10^8$ |
| E. coli 10121 | CTX-M-2 | 0.19 | 0.016 | 0.016 | $\geq 1 \times 10^8$ | $1 \times 10^1$ |
| E. coli FOR | CTX-M-15 | 0.12 | 0.012 | 0.012 | $\geq 1 \times 10^8$ | $1 \times 10^1$ |
| E. coli EVB | VEB-1 | 0.12 | 0.012 | 0.012 | $\geq 1 \times 10^8$ | $1 \times 10^1$ |
| E. coli 1092 | OXA-1 | 0.12 | 0.19 | 0.023 | $\geq 1 \times 10^8$ | $1 \times 10^1$ |
| E. coli ECA | ACC-1 | 0.12 | 0.012 | 0.012 | $\geq 1 \times 10^8$ | $5 \times 10^3$ |
| E. coli SYD | CMY-2 | 0.12 | 0.012 | 0.012 | $\geq 1 \times 10^8$ | $1 \times 10^1$ |
| E. coli MET | Chromosome-encoded extended-spectrum cephalosporinase | 0.12 | 0.012 | 0.012 | $\geq 1 \times 10^8$ | $1 \times 10^1$ |
| E. coli MAR[e] | Overexpressed AmpC | 16 | >32 | 2 | $1 \times 10^2$ | $1 \times 10^1$ |
| E. coli HB4[d] | (OmpC-, OmpF-) | 0.12 | 1 | 0.25 | $1 \times 10^1$ | $\geq 1 \times 10^8$ |
| E. aerogenes 1085 | TEM-24 | 0.12 | 0.19 | 0.023 | $\geq 1 \times 10^8$ | $1 \times 10^1$ |

TABLE 8-continued

Limit of detection of SUPERCARBA medium for 60 carbapenemase- and/or ESBL/AmpC-producing enterobacterial isolates as compared to those obtained with modified-SUPERCARBA, i.e. with oxacillin replacing cloxacillin. MIC values of imipenem, ertapenem and meropenem are provided for each strain.

| | | MIC (μg/ml) | | | Lowest detection limit (CFU/ml) | |
|---|---|---|---|---|---|---|
| Strains | -Lactamase content | IPM$^a$ | ETP | MEM | ETP Cloxa Zinc (SUPERCARBA) | ETP Oxa Zinc |
| E. cloacae 5434 | (wild type) | 0.38 | 0.016 | 0.032 | $>1 \times 10^8$ | $>1 \times 10^8$ |
| E. cloacae CLO | CTX-M-15 | 0.12 | 0.12 | 0.12 | $1 \times 10^7$ | $1 \times 10^1$ |
| E. cloacae 10111$^e$ | TEM-1 + CTX-M-15 | 0.5 | 0.75 | 0.094 | $>1 \times 10^8$ | $1 \times 10^1$ |
| E. cloacae CVB | VEB-1 | 0.12 | 0.12 | 0.12 | $1 \times 10^4$ | $1 \times 10^1$ |
| E. cloacae ARF$^e$ | Overexpressed AmpC | 0.12 | 1 | 0.12 | $1 \times 10^7$ | $1 \times 10^1$ |
| E. cloacae BLA$^e$ | Overexpressed AmpC | 0.12 | 1 | 0.12 | $1 \times 10^7$ | $1 \times 10^1$ |
| C. freundii 7767 | (wild type) | 0.25 | 0.008 | 0.016 | $>1 \times 10^8$ | $>1 \times 10^8$ |
| C. freundii 10107 | TEM-1 + SHV-12 | 0.38 | 0.016 | 0.023 | $>1 \times 10^8$ | $1 \times 10^1$ |
| C. freundii 10135 | CTX-M-15 | 0.38 | 0.016 | 0.023 | $>1 \times 10^8$ | $1 \times 10^1$ |
| C. freundii MAU$^e$ | Overexpressed AmpC + TEM-3 | 1 | 8 | 1 | $1 \times 10^5$ | $1 \times 10^1$ |
| S. typhimurium 1081 | CTX-M-1 | 0.25 | 0.19 | 0.032 | $>1 \times 10^8$ | $1 \times 10^1$ |
| P. mirabilis 1031 | CTX-M-14 + TEM-1 + SHV-11 | 1.5 | 0.047 | 0.032 | $>1 \times 10^8$ | $1 \times 10^1$ |
| P. mirabilis PMA | ACC-1 | 0.25 | 0.094 | 0.064 | $>1 \times 10^8$ | $>1 \times 10^8$ |

TABLE 9

Sensitivity and specificity of SUPERCARBA, ETP-Oxa-Zinc.$^a$

| | Detection medium | |
|---|---|---|
| | ETP Cloxa Zinc (SUPERCARBA) | ETP Oxa -Zinc |
| SN (%)$^a$ | 88 | 88 |
| SN class A$^b$ | 100 | 100 |
| SN class B | 40 | 40 |
| SN class D | 100 | 100 |
| SP (%) | 82.8 | 80 |

$^a$Abbreviations: SN, sensitivity; SP, specificity.
$^b$Sensitivity was determined for each Ambler class of carbapenemase.

TABLE 10

Limit of detection of SUPERCARBA medium (Drigalski + ETP + Cloxa + Zinc) for 51 carbapenemase- and/or ESBL/AmpC-producing enterobacterial isolates as compared to those obtained with modified-SUPERCARBA that contained Trypticase-soy agar replacing Drigalski agar supplemented with vancomycin (20 μg/ml) and ETP + Cloxa + Zinc. MIC values of imipenem, ertapenem and meropenem are provided for each strain.

| | | MIC (μg/ml) | | | Lowest detection limit (CFU/ml) | |
|---|---|---|---|---|---|---|
| Strains | -Lactamase content | IPM$^a$ | ETP | MEM | ETP Cloxa Zinc (SUPERCARBA) | ETP-Cloxa Zinc-Vanco-modified SUPERCARBA |
| Ambler class A carbapenemases (KPC) | | | | | | |
| K. pneumoniae MUS | KPC-2 + TEM-1 + SHV-11 + SHV-12 | 0.75 | 4 | 1.5 | $1 \times 10^1$ | $1 \times 10^1$ |
| E. cloacae HPTU | KPC-2 + TEM-1 + SHV-11 | 2 | 4 | 1.5 | $1 \times 10^1$ | $1 \times 10^1$ |
| Ambler class B carbapenemases | | | | | | |
| K. pneumoniae OMA419 | NDM-1 + OXA-1 | 1.5 | 6 | 2 | $1 \times 10^1$ | $1 \times 10^1$ |
| K. pneumoniae OM2 | NDM-1 + TEM-1 + CTX-M-3 + SHV-11 + OXA-1 | 0.75 | 8 | 1.5 | $1 \times 10^1$ | $1 \times 10^1$ |
| P. stuartii PS1 | NDM-1 + CMY-6 + OXA-1 | 12 | 0.38 | 1.5 | $1 \times 10^7$ | $1 \times 10^2$ |
| E. coli JAP | IMP-1 | 0.5 | 3 | 0.5 | $1 \times 10^4$ | $3 \times 10^1$ |
| E. cloacae TAW | IMP-8 + SHV-12 | 0.75 | 0.5 | 0.5 | $1 \times 10^2$ | $2 \times 10^2$ |

TABLE 10-continued

Limit of detection of SUPERCARBA medium (Drigalski + ETP + Cloxa + Zinc) for 51 carbapenemase-
and/or ESBL/AmpC-producing enterobacterial isolates as compared to those obtained with modified-SUPERCARBA
that contained Trypticase-soy agar replacing Drigalski agar supplemented with vancomycin (20 μg/ml)
and ETP + Cloxa + Zinc. MIC values of imipenem, ertapenem and meropenem are provided for each strain.

| Strains | -Lactamase content | MIC (μg/ml) IPM$^a$ | ETP | MEM | Lowest detection limit (CFU/ml) ETP Cloxa Zinc (SUPERCARBA) | ETP-Cloxa Zinc-Vanco-modified SUPERCARBA |
|---|---|---|---|---|---|---|
| Ambler class D carbapenemases | | | | | | |
| K. pneumoniae BEL | OXA-48 | 1 | 4 | 1 | $1 \times 10^1$ | $1 \times 10^1$ |
| K. pneumoniae SCO | OXA-48 | 0.5 | 0.75 | 0.25 | $1 \times 10^1$ | $1 \times 10^1$ |
| K. pneumoniae ROU | OXA-48 + CTX-M-15 | 0.5 | 1.5 | 0.25 | $1 \times 10^1$ | $1 \times 10^1$ |
| K. pneumoniae BAJ | OXA-48 + TEM-1 + CTX-M-15 + SHV-28 | 0.5 | 1.5 | 0.38 | $1 \times 10^1$ | $1 \times 10^1$ |
| K. pneumoniae BEN | OXA-48 + TEM-1 + CTX-M-15 + SHV-28 | 0.38 | 1 | 0.25 | $1 \times 10^1$ | $1 \times 10^1$ |
| K. pneumoniae SIC | OXA-48 + CTX-M-15 + SHV-28 | 0.25 | 1 | 0.25 | $1 \times 10^1$ | $1 \times 10^1$ |
| K. pneumoniae AMS | OXA-48 + TEM-1 + CTX-M-15 + OXA-1 | 0.5 | 2 | 0.38 | $1 \times 10^1$ | $1 \times 10^1$ |
| K. pneumoniae ELK | OXA-48 + TEM-1 + CTX-M-15 + SHV-11 | 0.5 | 3 | 0.38 | $1 \times 10^1$ | $1 \times 10^1$ |
| K. pneumoniae VSG | OXA-48 + TEM-1 + CTX-M-15 + OXA-1 | 0.75 | 3 | 0.75 | $1 \times 10^1$ | $1 \times 10^1$ |
| E. coli ROB | OXA-48 | 0.5 | 0.75 | 0.25 | $2 \times 10^1$ | $1 \times 10^1$ |
| E. coli BOU | OXA-48 + CTX-M-15 | 0.5 | 0.75 | 0.125 | $2 \times 10^1$ | $1 \times 10^1$ |
| E. coli AME | OXA-48 + CTX-M-24 | 0.25 | 0.5 | 0.19 | $2 \times 10^1$ | $1 \times 10^1$ |
| E. coli BON | OXA-48 + TEM-1 + CTX-M-24 | 0.38 | 0.5 | 0.19 | $1 \times 10^1$ | $1 \times 10^1$ |
| E. cloacae TUR | OXA-48 + SHV-5 | 0.5 | 0.5 | 0.5 | $1 \times 10^1$ | $1 \times 10^1$ |
| C. koseri VER | OXA-48 | 0.75 | 2 | 0.38 | $1 \times 10^1$ | $1 \times 10^1$ |
| K. pneumoniae HOL | OXA-181 + CTX-M-15 | 1 | 4 | 1 | $1 \times 10^1$ | $1 \times 10^2$ |
| K. pneumoniae OMA | OXA-181 + CTXM-15 + OXA-1 | 0.5 | 2 | 0.5 | $1 \times 10^1$ | $1 \times 10^1$ |
| P. rettgeri RAP | OXA-181 + OXA-1 | 8 | 1 | 2 | $5 \times 10^2$ | $1 \times 10^1$ |
| Non-carbapenemase producers | | | | | | |
| K. pneumoniae 7725 | SHV-1 | 0.19 | 0.006 | 0.032 | $\geq 1 \times 10^8$ | $\geq 1 \times 10^8$ |
| K. pneumoniae 648236$^d$ | SHV-2a | 0.25 | 2 | 0.38 | $1 \times 10^2$ | $3 \times 10^1$ |
| K. pneumoniae BER$^d$ | SHV-28 + TEM-1 | 1 | 4 | 1 | $1 \times 10^2$ | $1 \times 10^1$ |
| K. pneumoniae BED$^d$ | CTX-M-15 + TEM-1 + SHV-11 | 1.5 | >32 | 4 | $1 \times 10^1$ | $1 \times 10^1$ |
| K. pneumoniae ALE$^d$ | CTX-M-15 + SHV-1 | 1 | >32 | 4 | $1 \times 10^5$ | $1 \times 10^1$ |
| E. coli 1034 | TEM-1 + SHV-38 | 0.19 | 0.006 | 0.016 | $\geq 1 \times 10^8$ | $\geq 1 \times 10^8$ |
| E. coli 1048 | TEM-1 + SHV-2a | 0.19 | 0.012 | 0.016 | $\geq 1 \times 10^8$ | $\geq 1 \times 10^8$ |
| E. coli 1008 | TEM-1 + CTX-M-1 | 0.19 | 0.016 | 0.016 | $\geq 1 \times 10^8$ | $\geq 1 \times 10^8$ |
| E. coli 10121 | CTX-M-2 | 0.19 | 0.016 | 0.016 | $\geq 1 \times 10^8$ | $\geq 1 \times 10^8$ |
| E. coli FOR | CTX-M-15 | 0.12 | 0.012 | 0.012 | $\geq 1 \times 10^8$ | $\geq 1 \times 10^8$ |
| E. coli EVB | VEB-1 | 0.12 | 0.012 | 0.012 | $\geq 1 \times 10^8$ | $\geq 1 \times 10^8$ |
| E. coli ECA | ACC-1 | 0.12 | 0.012 | 0.012 | $\geq 1 \times 10^8$ | $\geq 1 \times 10^8$ |
| E. coli SYD | CMY-2 | 0.12 | 0.012 | 0.012 | $\geq 1 \times 10^8$ | $\geq 1 \times 10^8$ |
| E. coli MET | Chromosome-encoded extended-spectrum cephalosporinase | 0.12 | 0.012 | 0.012 | $\geq 1 \times 10^8$ | $\geq 1 \times 10^8$ |
| E. coli MAR$^e$ | Overexpressed AmpC | 16 | >32 | 2 | $1 \times 10^2$ | $\geq 1 \times 10^8$ |
| E. coli HB4$^d$ | (OmpC-, OmpF-) | 0.12 | 1 | 0.25 | $1 \times 10^1$ | $1 \times 10^1$ |
| E. aerogenes 1085 | TEM-24 | 0.12 | 0.19 | 0.023 | $\geq 1 \times 10^8$ | $\geq 1 \times 10^8$ |
| E. cloacae CLO | CTX-M-15 | 0.12 | 0.12 | 0.12 | $1 \times 10^7$ | $\geq 1 \times 10^8$ |
| E. cloacae 10111$^e$ | TEM-1 + CTX-M-15 | 0.5 | 0.75 | 0.094 | $\geq 1 \times 10^8$ | $2 \times 10^7$ |
| E. cloacae CVB | VEB-1 | 0.12 | 0.12 | 0.12 | $1 \times 10^4$ | $\geq 1 \times 10^8$ |
| E. cloacae CON$^e$ | Overexpressed AmpC | 0.12 | 1 | 0.12 | $1 \times 10^7$ | $1 \times 10^7$ |
| E. cloacae BLA$^e$ | Overexpressed AmpC | 0.12 | 1 | 0.12 | $1 \times 10^7$ | $2 \times 10^7$ |
| C. freundii 10107 | TEM-1 + SHV-12 | 0.38 | 0.016 | 0.023 | $\geq 1 \times 10^8$ | $\geq 1 \times 10^8$ |
| C. freundii 10135 | CTX-M-15 | 0.38 | 0.016 | 0.023 | $\geq 1 \times 10^8$ | $\geq 1 \times 10^8$ |
| C. freundii MAU$^e$ | Overexpressed AmpC + TEM-3 | 1 | 8 | 1 | $1 \times 10^5$ | $1 \times 10^1$ |
| S. typhimurium 1081 | CTX-M-1 | 0.25 | 0.19 | 0.032 | $\geq 1 \times 10^8$ | $\geq 1 \times 10^8$ |

TABLE 11

Sensitivity and specificity of SUPERCARBA
and modified SUPERCARBA screening media.

| | Detection medium | |
|---|---|---|
| | ETP Cloxa Zinc (SUPERCARBA) | Supercarba modified |
| SN (%)[a] | 92 | 100 |
| SP (%) | 80.8 | 77 |

[a]Abbreviations: SN, sensitivity; SP, specificity.

REFERENCES

Throughout this application, various references describe the state of the art to which this invention pertains. The disclosures of these references are hereby incorporated by reference into the present disclosure.

1. Castanheira, M., L. M. Deshpande, D. Mathai, J. M. Bell, R. N. Jones, and R. E. Mendes. 2011. Early dissemination of NDM-1- and OXA-181-producing *Enterobacteriaceae* in Indian hospitals: report from the SENTRY Antimicrobial Surveillance Program, 2006-2007. Antimicrob. Agents Chemother. 55:1274-1278.
2. Fukigai, S., J. Alba, S. Kimura, T. Iida, N. Nishikura, Y. Ishii, K. Yamaguchi. 2007. Nosocomial outbreak of genetically related IMP-1 beta-lactamase-producing *Klebsiella pneumoniae* in a general hospital in Japan. Int. J. Antimicrob. Agents. 29:306-310.
3. Lee, K., Y. S. Lim, D. Yong, J. H. Yum, and Y. Chong. 2003. Evaluation of the Hodge test and the imipenem-EDTA double-disk synergy test for differentiating metallo-β-lactamase-producing isolates of *Pseudomonas* spp. and *Acinetobacter* spp. J. Clin. Micobiol. 10: 4623-4629.
4. Nordmann, P., G. Cuzon, and T. Naas. 2009. The real threat of *Klebsiella pneumoniae* carbapenemase-producing bacteria. Lancet Infect. Dis. 9:228-236.
5. Nordmann, P., L. Poirel, M. A. Toleman, and T. Walsh. 2011. Does broad-spectrum resistance due to NDM-1 herald the end of the antibiotic era for treatment of infections caused by Gram-negative bacteria? J. Antimicrob. Chemother. 66:689-692.
6. Poirel, L., A. Ros, A. Carrër, N. Fortineau, A. Carricajo, P. Berthelot, and P. Nordmann. 2011. Cross-border transmission of OXA-48-producing *Enterobacter cloacae* from Morocco to France. J. Antimicrob. Chemother. 66:1181-1182.
7. Psichogiou, M., P. T. Tassios, A. Avlamis, I. Stefanou, C. Kosmidis, E. Platsouka, O. Paniara, A. Xanthaki, M. Toutouza, G. L. Daikos, and L. S. Tzouvelekis. 2008. Ongoing epidemic of bla$_{VIM-1}$-positive *Klebsiella pneumoniae* in Athens, Greece: a prospective survey. J. Antimicrob. Chemother. 61:59-63.
8. Cuzon, G., T. Naas, P. Bogaerts, Y. Glupczynski, T. D. Huang, and P. Nordmann. 2008. Plasmid-encoded carbapenem-hydrolyzing beta-lactamase OXA-48 in an imipenem-susceptible *Klebsiella pneumoniae* strain from Belgium. Antimicrob. Agents Chemother. 52:3463-3464.
9. Maltezou, H. C., P. Giakkoupi, A. Maragos, M. Bolikas, V. Raftopoulos, H. Papahatzaki, G. Vrouhos, V. Liakou, and A. C. Vatopoulos. 2009. Outbreak of infections due to KPC-2-producing *Klebsiella pneumoniae* in a hospital in Crete (Greece). J. Infect. 58:213-219.
10. Carrër, A., L. Poirel, H. Eraksoy, A. A. Cagatay, S. Badur, and P. Nordmann. 2008. Spread of OXA-48-positive carbapenem-resistant *Klebsiella pneumoniae* isolates in Istanbul, Turkey. Antimicrob. Agents Chemother. 52:2950-2954.
11. Carrër, A., L. Poirel, M. Yilmaz, O. A. Akan, C. Feriha, G. Cuzon, G. Matar, P. Honderlick, and P. Nordmann. 2010. Spread of OXA-48-encoding plasmid in Turkey. and beyond. Antimicrob. Agents Chemother. 54:1369-1373.
12. Carrër, A., N. Fortineau, and P. Nordmann. 2010. Use of ChromID extended-spectrum beta-lactamase medium for detecting carbapenemase-producing *Enterobacteriaceae*. J. Clin. Microbiol. 48:1913-1914.
13. Landman, D., J. K. Salvani, S. Bratu, and J. Quale. 2005. Evaluation of techniques for detection of carbapenem-resistant *Klebsiella pneumoniae* in stool surveillance cultures. J. Clin. Microbiol. 43:5639-5641.
14. Poirel, L., J. D. Pitout, and P. Nordmann. 2007. Carbapenemases: molecular diversity and clinical consequences. Future Microbiol. 2:501-512.
15. Queenan, A. M., and K. Bush. 2007. Carbapenemases: the versatile beta-lactamases. Clin. Microbiol. Rev. 20:440-458.
16. Réglier-Poupet, H., T. Naas, A. Carrer, A. Cady, J. M. Adam, N. Fortineau, C. Poyart, and P. Nordmann. 2008. Performance of chromID ESBL, a chromogenic medium for detection of *Enterobacteriaceae* producing extended-spectrum beta-lactamases. J. Med. Microbiol. 573:310-315.
17. Samra, Z., J. Bahar, L. Madar-Shapiro, N. Aziz, S. Israel, and J. Bishara. 2008. Evaluation of CHROMagar KPC for rapid detection of carbapenem-resistant *Enterobacteriaceae*. J. Clin. Microbiol. 46:3110-3111.
18. Bratu, S., M. Mooty, S, Nichani, D. Landman, C. Gullans, B. Pettinato, U. Karumudi, P. Tolaney, and J. Quale. 2005. Emergence of KPC-possessing *Klebsiella pneumoniae* in Brooklyn, N.Y.: epidemiology and recommendations for detection. Antimicrob. Agents Chemother. 49:3018-3020.
19. Doumith, M., M. J. Ellington, D. M. Livermore, and N. Woodford. 2009. Molecular mechanisms disrupting porin expression in ertapenem-resistant *Klebsiella* and *Enterobacter* spp. clinical isolates from the UK. J. Antimicrob. Chemother 63: 659-667.
20. Girlich, D., L. Poirel, and P. Nordmann. 2009. CTX-M expression and selection of ertapenem resistance in *Klebsiella pneumoniae* and *Escherichia coli*. Antimicrob. Agents Chemother. 53:832-834.
21. Jacoby, G. A., D. M. Mills, and N. Chow. 2004. Role of β-lactamases and porins in resistance to ertapenem and other β-lactams in *Klebsiella pneumoniae*. Antimicrob. Agents Chemother. 48: 3203-06.

The invention claimed is:

1. A method for detecting carbapenem-resistant bacteria in a test sample comprising the following successive steps:
   a) inoculating a culture medium with said test sample, wherein said culture medium comprises a carbapenem, a M-type penicillin and a carbapenemase activator selected from the group consisting of divalent cations and mixtures thereof, and is suitable for growth of class A, B and D carbapenemase-producing bacteria; and
   b) incubating said culture medium under conditions suitable for growth of carbapenem-resistant bacteria; and
   c) detecting colonies formed on said culture medium, wherein detection of colonies is an indication of the presence in said test sample of at least one species of carbapenem-resistant bacteria producing a carbapenemase belonging to class A, B or D.

2. The method according to claim 1, wherein the carbapenem is selected from the group consisting of ertapenem, biapenem, doripenem, imipenem, meropenem, tebipenem, panipenem and mixtures thereof.

3. The method according to claim 1, wherein the carbapenem is ertapenem and the concentration of ertapenem in the culture medium is from 0.1 to 1 µg/ml.

4. The method according to claim 1, wherein the carbapenem is doripenem and the concentration of doripenem in the culture medium is from 0.01 to 0.1 µg/ml.

5. The method according to claim 1, wherein the carbapenemase activator is a divalent cation selected from the group consisting of zinc, magnesium, manganese and mixtures thereof.

6. The method according to claim 1, wherein the divalent cation is zinc.

7. The method according to claim 1, wherein the M-type penicillin is selected from the group consisting of cloxacillin, dicloxacillin, flucloxacillin, oxacillin, methicillin, nafcillin and mixtures thereof.

8. The method according to claim 1, wherein the M-type penicillin is cloxacillin.

9. The method according claim 1, wherein the carbapenem is ertapenem, the divalent cation is zinc, and the M-type penicillin is cloxacillin.

\* \* \* \* \*